(12) United States Patent
Braig et al.

(10) Patent No.: US 6,944,486 B2
(45) Date of Patent: *Sep. 13, 2005

(54) METHOD AND APPARATUS FOR DETERMINING ANALYTE CONCENTRATION USING PHASE AND MAGNITUDE DETECTION OF A RADIATION TRANSFER FUNCTION

(75) Inventors: James R. Braig, Piedmont, CA (US); Charles E. Kramer, Poway, CA (US); Bernhard B. Sterling, Danville, CA (US); Daniel S. Goldberger, Boulder, CO (US); Peng Zheng, Alameda, CA (US); Arthur M. Shulenberger, Brisbane, CA (US); Rick Trembino, Atlanta, GA (US); Richard A. King, Berkeley, CA (US); Casper W. Barnes, Murrieta, CA (US)

(73) Assignee: Optiscan Biomedical Corporation, Alameda, CA (US)

(*) Notice: Subject to any disclaimer, the term of this patent is extended or adjusted under 35 U.S.C. 154(b) by 85 days.

This patent is subject to a terminal disclaimer.

(21) Appl. No.: 10/456,109

(22) Filed: Jun. 6, 2003

(65) Prior Publication Data

US 2004/0087841 A1 May 6, 2004

Related U.S. Application Data

(63) Continuation of application No. 09/538,164, filed on Mar. 30, 2000, now Pat. No. 6,580,934, which is a continuation-in-part of application No. 09/267,121, filed on Mar. 10, 1999, now Pat. No. 6,161,028, which is a continuation-in-part of application No. 08/820,378, filed on Mar. 12, 1997, now Pat. No. 5,900,632.

(51) Int. Cl.[7] .............................................. A61B 5/00
(52) U.S. Cl. .................. 600/310; 600/322; 250/339.03; 250/339.07; 250/341.6
(58) Field of Search .................................. 600/309, 310, 600/316, 322, 473, 474; 250/341.6, 341.1, 341.5, 339.07, 339.09, 339.03, 339.04, 339.05, 339.12

(56) References Cited

U.S. PATENT DOCUMENTS

| | | |
|---|---|---|
| 3,958,560 A | 5/1976 | March |
| 4,429,999 A | 2/1984 | Bimberg et al. |
| 4,655,225 A | 4/1987 | Dahne et al. |

(Continued)

FOREIGN PATENT DOCUMENTS

| | | |
|---|---|---|
| CH | 612271 | 7/1979 |
| WO | WO 91/15992 | 10/1991 |
| WO | WO 92/10131 | 6/1992 |

(Continued)

OTHER PUBLICATIONS

A.S. Glushkov, Thermoptical converter with liquid modulating medium, Sov. Tech. Phys. Lett. 5(10), p. 512 (Oct. 1979).

(Continued)

Primary Examiner—Eric F. Winakur
(74) Attorney, Agent, or Firm—Knobbe, Martens, Olson & Bear LLP

(57) ABSTRACT

A method and apparatus of determining the analyte concentration of a test sample is described. A temperature gradient is introduced into the test sample and infrared radiation detectors measure radiation at selected analyte absorbance peak and reference wavelengths. The modulation of the temperature gradient is controlled by a surface temperature modulation. A transfer function is determined that relates the surface temperature modulation to the modulation of the measured infrared radiation. Reference and analytical signals are detected. In the presence of the selected analyte, phase and magnitude differences in the transfer function are detected. These phase and magnitude differences, having a relationship to analyte concentration, are measured, correlated and processed to determine analyte concentration in the sample.

27 Claims, 24 Drawing Sheets

U.S. PATENT DOCUMENTS

| | | | |
|---|---|---|---|
| 4,926,867 A | 5/1990 | Kanda et al. | |
| 5,009,230 A | 4/1991 | Hutchinson | |
| 5,040,539 A | 8/1991 | Schmitt et al. | |
| 5,070,242 A | 12/1991 | McClelland et al. | |
| 5,075,552 A | 12/1991 | McClelland et al. | |
| 5,122,974 A | 6/1992 | Chance | |
| 5,137,023 A | 8/1992 | Mendelson et al. | |
| 5,187,672 A | 2/1993 | Chance et al. | |
| 5,191,215 A | 3/1993 | McClelland et al. | |
| 5,209,231 A | 5/1993 | Cote et al. | |
| 5,313,941 A | 5/1994 | Braig et al. | |
| 5,348,003 A | 9/1994 | Caro | |
| 5,360,004 A | 11/1994 | Purdy et al. | |
| 5,361,758 A | 11/1994 | Hall et al. | |
| 5,370,114 A | 12/1994 | Wong et al. | |
| 5,372,135 A | 12/1994 | Mendelson et al. | |
| 5,372,136 A | 12/1994 | Steuer et al. | |
| 5,383,452 A | 1/1995 | Buchert | |
| 5,451,787 A | 9/1995 | Taylor | |
| 5,461,229 A | 10/1995 | Sauter et al. | |
| 5,471,056 A | 11/1995 | Prelat | |
| 5,473,162 A | 12/1995 | Busch et al. | |
| 5,492,118 A | 2/1996 | Gratton et al. | |
| 5,515,847 A | 5/1996 | Braig et al. | |
| 5,615,672 A | 4/1997 | Braig et al. | |
| 5,666,956 A | 9/1997 | Buchert | |
| 5,676,143 A | 10/1997 | Simonsen et al. | |
| 5,692,503 A | 12/1997 | Kuenstner | |
| 5,755,226 A | 5/1998 | Essenpreis et al. | |
| 5,770,454 A | 6/1998 | Carim et al. | |
| 5,823,677 A | 10/1998 | Forester et al. | |
| 5,900,632 A | 5/1999 | Sterling et al. | |
| 6,002,953 A | 12/1999 | Block | |
| 6,016,435 A | 1/2000 | Maruo et al. | |
| 6,580,934 B1 * | 6/2003 | Braig et al. ................. | 600/310 |
| 2002/0026106 A1 | 2/2002 | Khalil et al. | |

FOREIGN PATENT DOCUMENTS

| | | |
|---|---|---|
| WO | WO 93/00855 | 1/1993 |
| WO | WO 93/13706 | 7/1993 |
| WO | WO 94/13199 | 6/1994 |
| WO | WO 95/20757 | 8/1995 |
| WO | WO 96/01075 | 1/1996 |
| WO | WO 99/55222 | 11/1999 |

OTHER PUBLICATIONS

Barnes, Barnes Infrared Camera, Defense and Space Division Bames Engineering Co. Bulletin, 12–600, pp. 1–12 (May 1963).

Dueker et al., Germanium Nonscanned Infrared Imager, IEEE Transaction on Electron Devices, vol. ED–18, No. 11, pp. 1108–1112 (Nov. 1991).

F.G. Pollack, Advanced in Turbine Blade Temperature Measurements $22^{nd}$ Int'l Instrumentation Symposium, San Diego CA, ISA ASI 76256, pp. 393–398 (May 1976).

Halliday et al., Fundamentals of Physics, $2^{nd}$ Ed. 1981, pp. 358–361.

O. Guillois, I. Nenner, R. Papoular, & C. Reynaud, IR Emission Spectrum of Solid Materials Under Periodic Heating; Modulcated Emission Spectroscopy (MES), Applied Spectroscopy, vol. 48, No. 3, pp. 297–306 Mar., 1994).

R. Bowling Barnes, Thermography of the Human Body, Science, May 24, 1963, vol. 140, No. 3569, pp. 870–877.

Roger W. Jones & John R. McClelland, on–line analysis of solids and viscous liquids by transient infrared spectroscopy, Process Control and Quality, 1993, pp. 253–260.

Roger W. Johns & John R. McClelland, Transient Intrared Transmission Spectroscopy, Analytic Chemistry, 1990.

Roger W. Jones & John F. McClelland, Quantitative Analysis of Solids in Motion By Transient Infrared Emission Spectroscopy Using Hot–Gas Jet Excitation, Analytic Chemistry, 1990.

Roger W. Jones & John F. McClelland, Real–Time Infrared Spectroscopy of Moving Solids for On–Line Analysis, 1991.

* cited by examiner

METHOD AND APPARATUS FOR DETERMINING ANALYTE CONCENTRATION USING PHASE AND MAGNITUDE DETECTION OF A RADIATION TRANSFER FUNCTION

RELATED APPLICATION

This application is a continuation of application Ser. No. 09/538,164 (now U.S. Pat. No. 6,580,934), filed 30 Mar. 2000, which is a continuation-in-part of application Ser. No. 09/267,121 (now U.S. Pat. No. 6,161,028), filed 10 Mar. 1999, which is a continuation-in-part of application Ser. No. 08/820,378 (now U.S. Pat. No. 5,900,632), filed 12 Mar. 1997. Each patent and patent application referenced in the preceding sentence is hereby incorporated by reference herein in its entirety. Furthermore, this application is related to, and incorporates by reference, the application entitled "Solid-state Non-invasive Infrared Absorption Spectrometer for the Generation and Capture of Thermal Gradient Spectra from Living Tissue," U.S. patent application Ser. No. 09/265,195, filed Mar. 10, 1999.

FIELD OF INVENTION

This invention relates to methods of determining the presence and concentration of analytes in a test sample. More specifically, the present invention relates to methods for non-invasively determining the analyte concentrations in human or animal subjects. Most specifically, the present invention relates to non-invasive methods for the determination of blood glucose concentration in a human patient.

BACKGROUND OF THE INVENTION

The analysis of samples and the determination of the presence or concentration of chemical species contained therein is a common and important process in chemistry and biology. Particularly important is the analysis of biological fluids, such as blood, urine, or saliva, to determine the concentration of various constituents. Also of great importance is the measurement of the concentration of various chemical constituents embedded within biological materials, such as tissue. Chemical analysis of blood, urine, and other biological fluids is crucial to the diagnosis, management, treatment, and care of a wide variety of diseases and medical conditions. In the case of diabetes, monitoring of blood glucose levels several times a day is necessary to the efficient management of this disease in many patients. Analysis of various blood components is of importance in both the diagnosis and treatment of diseases of the circulatory system. For example, the level of various types of cholesterol in the blood has a strong correlation with the onset of heart disease. Urine analysis provides valuable information relating to kidney function and kidney disease. The concentration of alcohol in the blood is known to be related to a subject's physical response time and coordination and can provide information related to, for example, the individual's fitness to drive a motor vehicle.

Additionally, there are many instances where it is desirable to measure the local concentration of chemical constituents in tissue, either in-vivo or in-vitro. For example, in stroke victims it is important to monitor the degree of brain edema or the concentration of various metabolic chemical constituents in the brain that serve as indicators of brain function. Such indicators include fatty acid compounds, water, blood, lactates, and certain proteins and lipids. Other specific examples may include the monitoring of tissue oxygenation or tissue blood perfusion as a means to of gauging the metabolic function of a human or animal subject.

Moreover, in many applications, a "real-time" measurement of chemical concentration in biological fluids is important Current invasive methods require that a sample of fluid be removed from a subject and then analyzed in one or more chemical tests. The tests can be expensive and require skilled technicians to remove and analyze the samples. Furthermore, the analysis of samples may have an undesirably long turn-around time. Additionally, the tests are usually made in centralized clinical laboratories with a resulting complexity of sample tracking and quality control. These circumstances create additional problems related to the potential change in the chemical composition of the fluid between extraction and analysis and, even more detrimentally, the possibility of a sample being confused with the samples of other patients.

It is also advantageous to analyze the chemical nature of sample materials without physically extracting a sample from the subject. For example, it is advantageous to examine the chemical makeup of human blood without taking a blood sample. In addition to time and cost considerations such invasive testing causes skin trauma, pain, and generates blood waste.

For all of the foregoing reasons methods of "non-invasive" testing have long been considered an attractive alternative to invasive testing. However, prior non-invasive testing methods have suffered from a number of practical drawbacks. The present invention is a method of analytical and quantitative testing for the presence of chemical species in a test sample. The method is non-invasive and has wide utility, being easily applicable to the non-invasive measurement of humans, animals, plants, or even packaged materials. Being highly versatile the method is broadly applicable to both in-vivo and in-vitro samples.

1. Brief Description of the Related Art

The concept of non-invasive testing is not unknown in the art. What has been elusive is the ability of quickly, easily, cheaply and accurately conducting measurements.

Certain infrared (IR) detection techniques are known and have been used to detect the presence of chemical constituents in the blood. Specific examples include the IR detection of oxygen saturation, nitrous oxide concentration, carbon dioxide concentration, or measurement of oxidative metabolism, and blood glucose levels. The goal of these inventions is the determination of human blood chemistry. A typical present technology projects light into the body while measuring the light after it passes through the body. Comparing the input beam with an exit beam allows a rough determination of blood chemistry. Unfortunately, these techniques suffer from a number of inadequacies, most especially, tissue interference, lack of specificity, and limited accuracy. A number of prior art patents describing such techniques are set forth below.

Kaiser describes, in Swiss Patent No. 612,271, a technique for using an IR laser as a radiation source to measure glucose concentrations in a measuring cell. This technique uses venous blood passed through extra-corporeal cuvettes at high blood flow rates. This has the undesirable effect of heating the blood and requiring that the blood be removed from the patient's body. Kaiser does not describe a non-invasive technique for measuring glucose concentration.

March, in U.S. Pat. No. 3,958,560, describes a "noninvasive" automatic glucose sensor system which projects polarized IR light into the cornea of the eye. A sensor detects the rotation of this polarized IR light as it passes between the eyelid and the cornea. The rotation of polarized light is correlated to glucose concentration. Although this technique does not require the withdrawal of blood, and is thus, "noninvasive", the device may cause considerable discomfort to the patient due to the need to place it on the patient's eye. Furthermore, March does not use an induced temperature gradient or absorbance spectroscopy as does the present invention. As a result, the present invention involves no physical discomfort and is more accurate.

Hutchinson, in U.S. Pat. No. 5,009,230, describes a glucose monitor which uses polarized IR light to non-invasively detect glucose concentration in a person's blood stream, The method requires an external IR source, which is passed through a portion of the human body. However, the accuracy of measurement is limited by the wavelengths of the polarized light beam (940–1000 nm) being used. Unlike the present invention, Hutchinson relies on detected changes in the polarization of the incident light beam. Furthermore, Hutchinson does not use an induced temperature gradient as does the present invention.

Similar limitations are found in Daline, et al., in U.S. Pat. No. 4,655,225, which describes a similar spectrophotometric technique. Dahne uses a directional external IR radiation source to emit a beam. Reflected and transmitted light from the beam is used to determine the glucose concentration Daline differs from other techniques in using radiation at wavelengths between 1000–2500 nm. Unlike Dahne, the present invention is not confined to using wavelengths, between 1000–2500 nm. Dahne also does not use an induced temperature gradient as does the present invention.

Mendelson, et al., in U.S. Pat. No. 5,137,023, uses a different concept known as pulsatile photoplethysmography to detect blood analyte concentration. The instrument of Mendelson is based on the principles of light transmission and reflection photoplethysmography, whereby analyte measurements are made by analyzing either the differences or ratios between two different IR radiation sources that are transmitted through an appendage or reflected from tissue surface before or after blood volume change occurs in response to systolic and diastolic phases of the cardiac cycle. Once again, the technique requires the use of external IR sources and is susceptible to interference from body tissue and other blood compounds.

Rosenthal, et at., in U.S. Pat. No. 5,028,787, discloses a non-invasive blood glucose monitor which also uses IR energy in the near IR range (600–1100 nm) to measure glucose. As with the above-mentioned devices, these wavelengths suffer from poor analyte absorption which results in poor resolution and insufficient specificity.

Cho, et al., in PCT No. PCT/DE95/00864, discloses a blood glucose monitor which uses heat flux generated in a patients fingertip to measure metabolic rate. Indirectly, this approximation of metabolic rate is used to measure approximate glucose concentration.

Major steps forward are embodied in the glucose measuring techniques disclosed in the patents to Braig, et al., U.S. Pat. No. 5,313,941 ('941). However, the '941 patent requires an independent external IR source to determine blood analyte concentration.

Optiscan, Inc of Alameda, Calif. has expanded the concept of gradient absorbance spectroscopy and demonstrated the utility of non-invasively measuring differential absorbance to determine blood glucose concentration in human subjects in U.S. patent application Ser. Nos. 08/816,723 and 08/820,378, both of which are hereby incorporated by reference.

2. Scientific Background of the Invention.

An understanding of the present invention requires an understanding of the concepts of transmission spectroscopy and gradient spectroscopy.

Basic transmission spectroscopy identifies analytes (an analyte is defined as a chemical species sought to be identified by the present invention) by comparing a light beam passed through a test sample to a reference beam not passed through the sample. Typically, transmission spectroscopy requires the test sample be removed from its native environment to a sample holder for analysis. The absorbance spectrum of the sample is examined. At specific wavelengths (known as analyte absorbance peaks) the light from the beams are compared. By using Beer's Law and comparing the sample beam with the reference beam in selected absorbance regions the absorbance of a sample may be measured and a determination of analyte concentration may be made. This is known as classical transmission cell spectroscopy. Strictly speaking, this method is unsuitable for non-invasive measurement. Significant problems being the need for extracting samples and the inability to accurately determine the pathlength of the beams used to analyze in-vivo samples. Progress has been made in overcoming these limitations as shown in the patents to Braig, et al., in U.S. Pat. Nos. 5,313,941, 5,515,847, and 5,615,672 and in U.S. patent applications Ser. Nos. 08/816,723 and 08/820,378. These patents and patent applications have laid the groundwork for the novel advances embodied in the present invention and are hereby incorporated by reference.

An understanding of the radiation emission characteristics of matter are also needed. All objects at a temperature greater than 0 K emit electromagnetic radiation in the form of photons. Ideal blackbody radiators (objects having an emissivity coefficient $e_m=1.0$) radiate energy according to the Stefan-Boltzmann Law and Planck's Equation (i.e. radiation output increases with increasing temperature). Additionally, many non-blackbody objects demonstrate near-blackbody radiation characteristics. For example, the human body's spectral radiation characteristics are very similar to that of a blackbody radiator and may be described as a "graybody" distribution (for example, having an en, of about 0.9). These radiative characteristics provide known sources of IR radiation which may be used to non-invasively analyze the constituents of a test sample.

Furthermore, an analysis of radiation behavior shows that, in objects at a constant and uniform temperature, photons emitted from the interior of the object are reabsorbed within 10–20 $\mu$m of the point of origin. Thus, an external radiation detector cannot detect radiation emitted from deeper than 20 $\mu$m inside an object. Under these conditions, only an object's surface emission spectrum is detectable by a detector. This poses a significant problem for non-invasive measurement techniques seeking to analyze chemical characteristics present deeper within an object.

The field of gradient spectroscopy was developed, in part, in an attempt to overcome the photon reabsorption problem. The Optiscan patent applications Ser. Nos. 08/816,723 and 08/820,378 disclose a thermal gradient, induced by a single temperature event and a measurement of differences in signal magnitude to non-invasively measure human test samples. The Optiscan applications use a temperature gradient induced by a single temperature event to non-invasively determine the glucose concentration in a human test subject by analyzing differences in signal magnitude at selected wavelengths.

Briefly, in the context of the present invention, a temperature gradient exists where the temperature of a material varies according to some arbitrary function, usually related to depth or time or both. For example, if some material is at an initial temperature (e.g., 37° C.) and a surface of the material is cooled to some lower temperature (e.g., 10° C.)

a gradient is induced in the material with the cooled surface being at approximately 10° C. and the deeper (and as yet unaffected) regions being at approximately 37° C. A temperature gradient exists between the two extremes.

The total radiation reaching the surface is the sum of weighted radiation coming from all depths below the surface. The weight given to radiation from a given depth depends on the absorbance of the medium between that depth and the surface. At any particular wavelength, this radiation weighting function decrease exponential-like with depth. If the medium is at a uniform temperature, T, then all depths will be radiating reaching the surface will have a Planck spectrum for temperature T. However, if the temperature below the surface is cooler (or hotter) than the surface, then the contribution to the total radiation from this cooler (or hotter) region will have a different spectrum than the surface radiation. Thus, the total radiation will not have a spectrum corresponding to either temperature, but will be something in between, depending on the relative contributions from the regions of different temperature.

SUMMARY OF THE INVENTION

Accordingly, an object of the present invention is to provide a new and improved method for detecting and quantifying various chemical analytes present within a test sample. In particular, an object of the present invention is to determine the absolute or relative concentration of chemical species contained in a test sample medium. Another object of the present invention to provide a non-invasive method of quantifying various chemical analytes within biological media.

A specific object of the invention is to provide a new and improved method for measuring the concentration in human, animal, and plant subjects of chemical species, such as glucose, insulin, water, carbon dioxide, alcohol, blood oxygen, cholesterol, bilirubin, ketones, fatty acids, lipoproteins, albumin, urea, creatinine, cytochrome, various proteins and chromophores, microcalcifications, and hormones, white blood cells, red blood cells, hemoglobin, oxygenated hemoglobin, carboxyhemoglobin, organic molecules, inorganic molecules, and inorganic molecules, such as phosphorus or various drugs and pharmaceuticals in blood, urine, saliva, or other body fluids. A further object of the invention is to make such/measurements non-invasively, quickly, easily, and with extreme accuracy.

The present invention describes a method for quantitatively determining the chemical composition of a test sample. Test samples may be chosen from a broad range of in-vivo or in-vitro samples. The present method uses a radiation detector, a data processing means, and a means for inducing a periodic thermal gradient in the test sample. The method generally comprises the steps of providing a test sample, inducing a thermal gradient in the sample, using the detector for measuring analytical signals from the sample at one or more predetermined wavelengths. Simultaneously, one or more reference signals are measured at reference wavelengths. The analytical and reference signals are compared to determine a parameter. The parameter may be phase difference or signal amplitude difference. The parameter information is correlated with empirically determined analyte concentration information by the data processing means, thereby determining the analyte concentration of the sample. This information is transmitted as an electrical signal for further processing.

A particularly useful parameter is a measurement of the phase difference (or phase delay) between said analytical and one or more of said reference signals. The magnitude of the phase difference is correlated with data stored in a data processing means to determine analyte concentration.

The accuracy of the method is substantially enhanced by inducing a periodically modulated temperature gradient in the sample, measuring the reference and analytical signals, continuously monitoring the parameters between the reference and analytical signals, and then integrating the parameter information over a test period. Correlation of this information with empirically determined analyte concentration information allows the analyte concentration of the sample to be determined and transmitted as an electrical signal for further processing.

Alternatively, when using a periodically modulated temperature gradient and phase difference information, the phase may be monitored at reference and analytical phase signal "zero crossings" to determine phase delay and thereby determine analyte concentration.

Additionally, the present method may be used to monitor analyte concentration at varying depths inside a test sample. This is accomplished by introducing two or more periodic temperature gradients in a sample at two or more driving frequencies. The resulting signals are processed to extract phase information and determine analyte concentration at varying depths within a sample. This has particular usefulness in analyzing analyte concentrations in test samples having non-uniform properties.

According to another alternative a transfer function relating to a temperature modulation at the surface of the sample with the modulation of the radiation emitted from the sample over a number of wavelengths is determined. By monitoring the phase and magnitude of this transfer function an absorbance is determined at different wavelengths and the concentration of an analyte is determined.

According to a further alternative a number of model transfer functions are stored at a central location, for example, a file server connected with a telecommunication network, such as the Internet. Each of these model transfer functions corresponds to a particular sample type, for example the tissue of a human subject with a particular set of physical characteristics. A human subject, for example, a person with diabetes, then selects a model transfer function based on his own physical characteristics to most closely match his own tissues. The selected transfer function is then used by a device according to the present invention to determine the concentration of glucose in the patient's tissue.

Other features of the invention are disclosed or made apparent in the section entitled "Detailed Description of the Invention".

BRIEF DESCRIPTION OF DRAWINGS

For a fuller understanding of the present invention, reference is made to the accompanying drawings, which detail various aspects of the invention.

Reference numbers refer to the same or equivalent parts of the invention throughout the several figures of the drawings.

DETAILED DESCRIPTION OF THE INVENTION

The present invention goes beyond the existing art by advantageously exploiting phase effects caused by induced temperature gradients to determine analyte concentration. The following example illustrates the general principles of the present invention.

A test sample containing analytes is provided. The term "test sample" shall be interpreted broadly to include any type of analytical sample. In its most basic form the sample comprises a sample medium and the chemical analytes contained therein. The term medium is broad in its application. The medium may be comprised of solids or fluids or any combination thereof. The medium may comprise biological material.

The present method may be applied to any type of material ordinarily analyzed using transmission cell spectroscopy. Biological materials such as human, animal, or plant material may be analyzed. These biological samples may be analyzed, either in-vivo or in-vitro. The method is versatile and may be applied to a wide range of samples, including but not limited to, in-vivo blood samples or in-vivo analysis of fruit contents, for example, testing grapes remaining on the vine for sugar content. Although most advantageously used, as a method for non-invasively measuring analyte concentrations in living subjects, the method finds utility as a method for analyzing invasively removed samples such as blood or saliva removed from a subject and placed in a glass cuvette for analysis. The device may even be used to determine analyte concentrations in packaged meats without opening a plastic wrapper.

The method of the present invention requires an induced temperature gradient and monitoring of radiation emitted from test samples. A satisfactory means for meeting this requirement is described in U.S. patent application Ser. No. 09/265,195 entitled "Solid-state Non-invasive Infrared Absorption Spectrometer for the Generation and Capture of Thermal Gradient Spectra from Living Tissue," filed Mar. 10, 1999.

Figure 1:
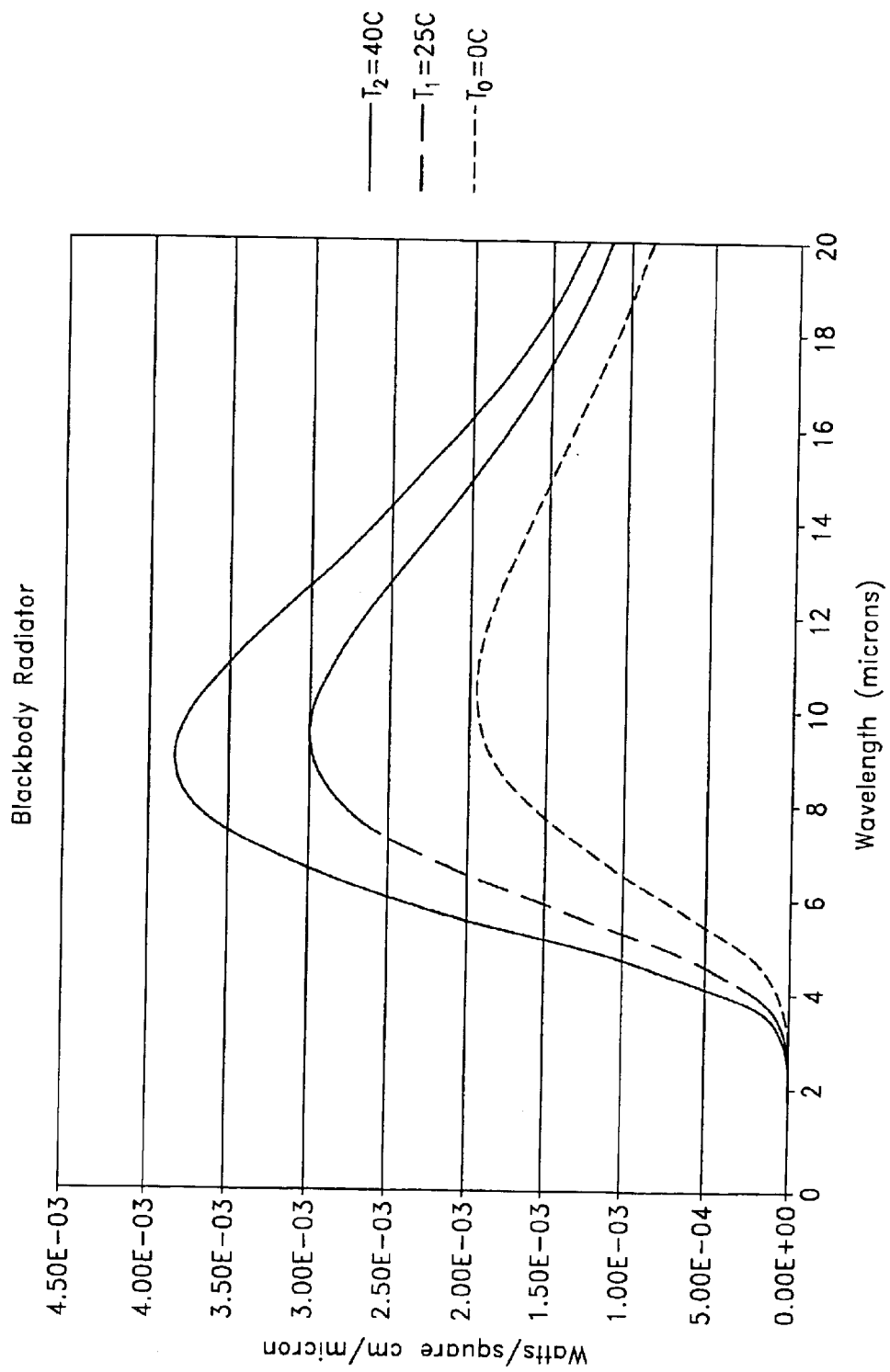
FIG. 1 is a graphical representation of the temperature effect on a blackbody radiator in units of emitted energy at a given wavelength.
Figure 2:
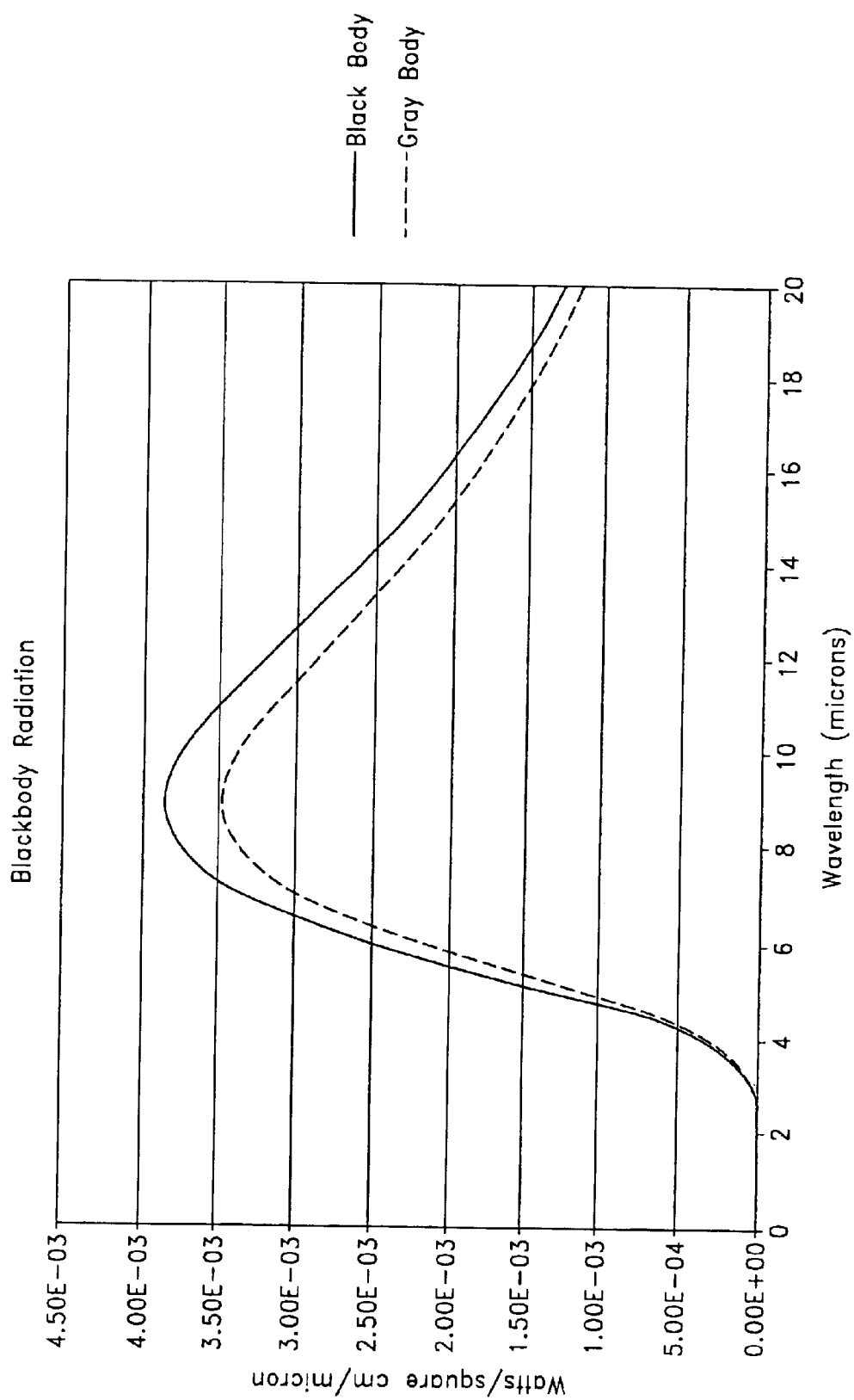
FIG. 2 is a graphical comparison of a true blackbody radiation spectrum with the emission spectrum of a human body, given in units of emitted energy at a given wavelength.

FIG. 1 shows the radiation distribution of a blackbody radiator ($e_m$=1) in comparison to a "graybody" radiator (e.g. human skin; em of approximately 0.9). FIG. 2 shows the effect of temperature on spectral radiation emitted from the same body at increasing temperatures $T_0$, $T_1$, and $T_2$.

Figure 3:
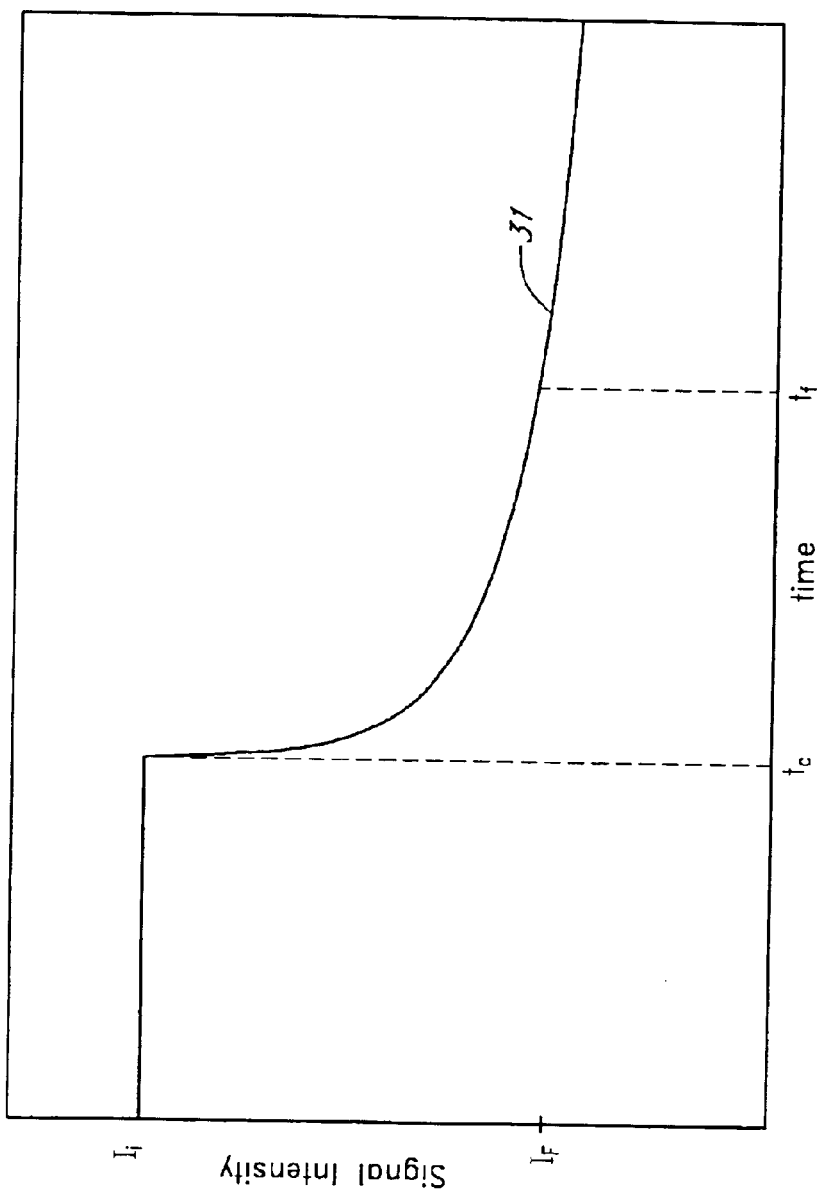
FIG. 3 is a graphical representation of detector signal response to an induced temperature gradient with the y-axis representing detector signal intensity and the x-axis representing time.

FIG. 3 graphically depicts a radiation detector output 31 of a typical sample monitored over time. Prior to inducing a temperature event, no gradient exists in the sample. Using a uniformly warm test sample at an initial temperature $T_i$, a detector signal 31 of constant intensity $I_i$ is measured. Without a temperature gradient, the signal 31 remains at a constant intensity $I_i$.

By subjecting a sample to a temperature event, a temperature gradient is produced. To induce a gradient, the temperature event must be either cooler or warmer than the temperature $T_i$ of the sample. Either one works equally well. FIG. 3 illustrates the principle as applied to a cooling event. A cooling temperature $T_C$ is induced in the sample at a time $t_C$. Subsequently, the temperature of the sample begins to drop, resulting in a lower detector signal 31. At some later time $t_F$, the temperature reaches a new (and lower) equilibrium temperature, resulting in a lower detector signal 31 having intensity $I_F$. The opposite would be true if the sample was heated, resulting in a higher final equilibrium temperature and higher output signal intensity.

Another aspect of the surface cooling event is that, although the surface itself cools almost immediately due to its close physical proximity to the cooling event, the underlying regions, being further from the cooling source, cool somewhat more slowly. This phenomenon is schematically depicted in FIGS. 4(I)(a) through 4(IV)(b). FIG. 4(I)(a) depicts a typical sample material 40 prior to inducing a temperature event. The sample 40 depicted is at an arbitrarily warm uniform temperature $T_i$ (e.g., 30° C.). This means that the surface S of the sample 40 is at or about 30° C. and the interior d of the sample 40 is still at $T_i$ (about 30° C.) and no gradient is present. As shown in FIG. 4(I)(b), if no temperature event is induced in the sample 40, the temperature of the sample remains constant, no gradient exists, and a constant detector signal 31 is observed at an initial signal intensity $I_i$.

Figure 4:
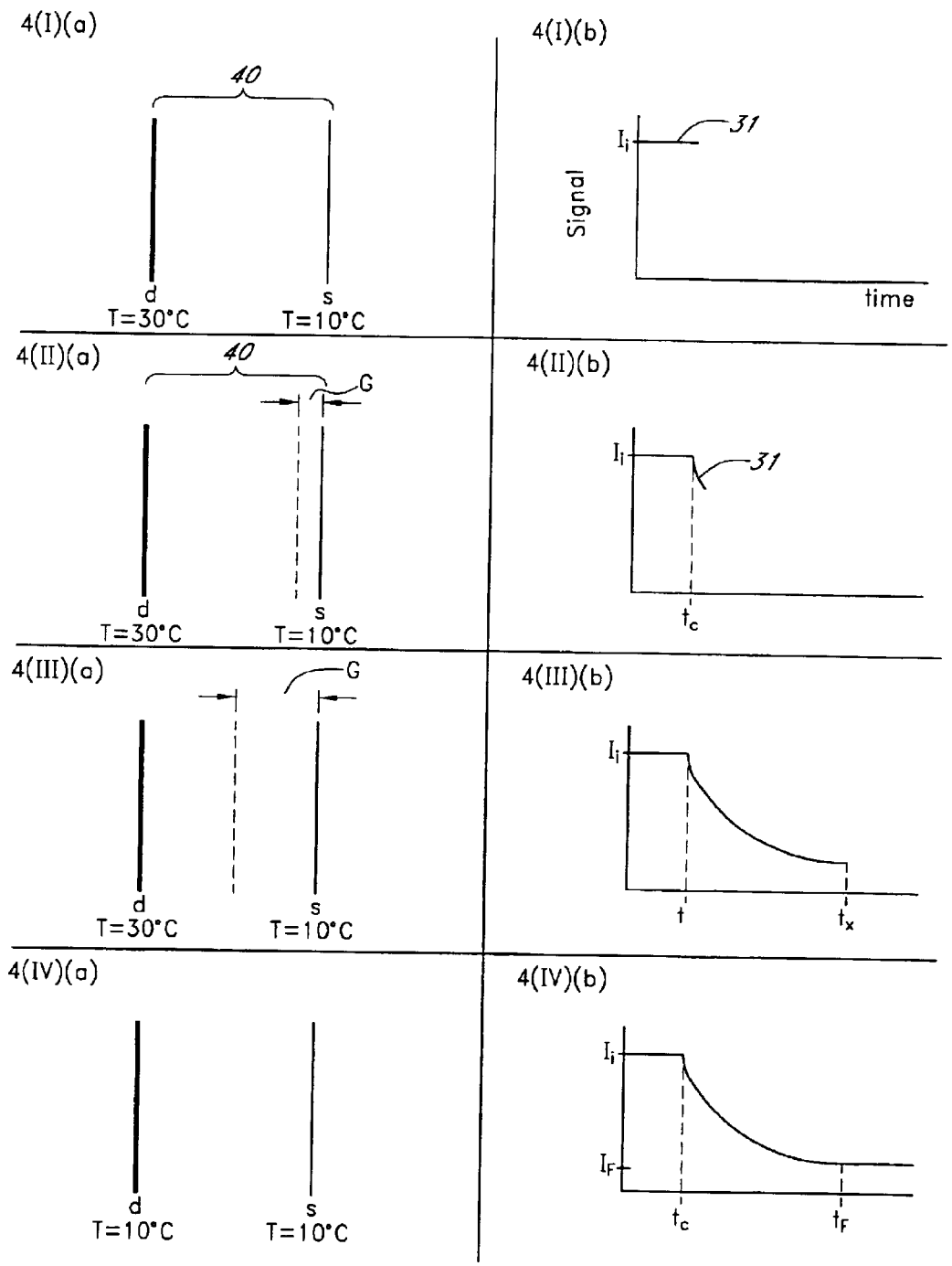
FIGS. 4(I)(a) through 4(IV)(b) are schematic diagrams showing the effect of a thermal gradient on radiation emitted from the skin's surface. The (a) series of Figures depict gradient effects in a physical test sample material. The (b) series of Figures are graphical depictions of the gradient effects as functions of detector signal and time.

Referring to FIGS. 4(II)(a) and 4(II)(b), if at some later time $t_C$ the surface is subject to a cooling event (for example using a cooling event temperature $T_C$ of 10° C.), this situation begins to change. At first only the surface cools (shown as 10° C.), the rest of the sample remaining at an initial temperature $T_i$ (e.g. 30° C.). Just underneath the surface S, the sample begins to cool slightly from the initial temperature (30° C.). This results in a small temperature gradient G. This decline in temperature is accompanied by a decline in detector output signal 31 as shown in FIG. 4(II)(b).

FIGS. 4(III)(a) and 4(III)(b) show the effects of the cooling event after some time $t_x$. Under the continued influence of the cooling event, the deeper regions of the sample continue to cool, enlarging the depth and magnitude of the gradient G. As the temperature of the sample 40 cools and the gradient increases, the detector signal 31 falls off, reflecting the effects of the declining temperature. As is obvious from the example above, the gradient effect is time dependent. Meaning, the longer the surface S is subjected to the cooling event, the colder the deeper regions of the sample will become. The lower limit on temperature being dictated by the temperature $T_C$ of the temperature event. Over time, the gradient G expands into the deeper regions of the sample 40. This creates a time-dependent temperature gradient in the sample.

Finally, as shown in FIGS. 4(IV)(a) and 4(IV)(b), the sample 40 reaches a new cooler steady state temperature (e.g. 10° C.) and the gradient G disappears. Consequently, the detected signal 31 from the sample 40 equilibrates at a new, lower level $I_F$.

The time-varying nature of the temperature gradient may be exploited in a novel way to determine the concentration of various analytes contained in a test sample. By combining the effects of an induced temperature gradient with the principles of transmission cell spectroscopy, the present invention embodies an extremely accurate and non-invasive method of determining analyte concentration, which goes far beyond existing technologies.

Figure 5:
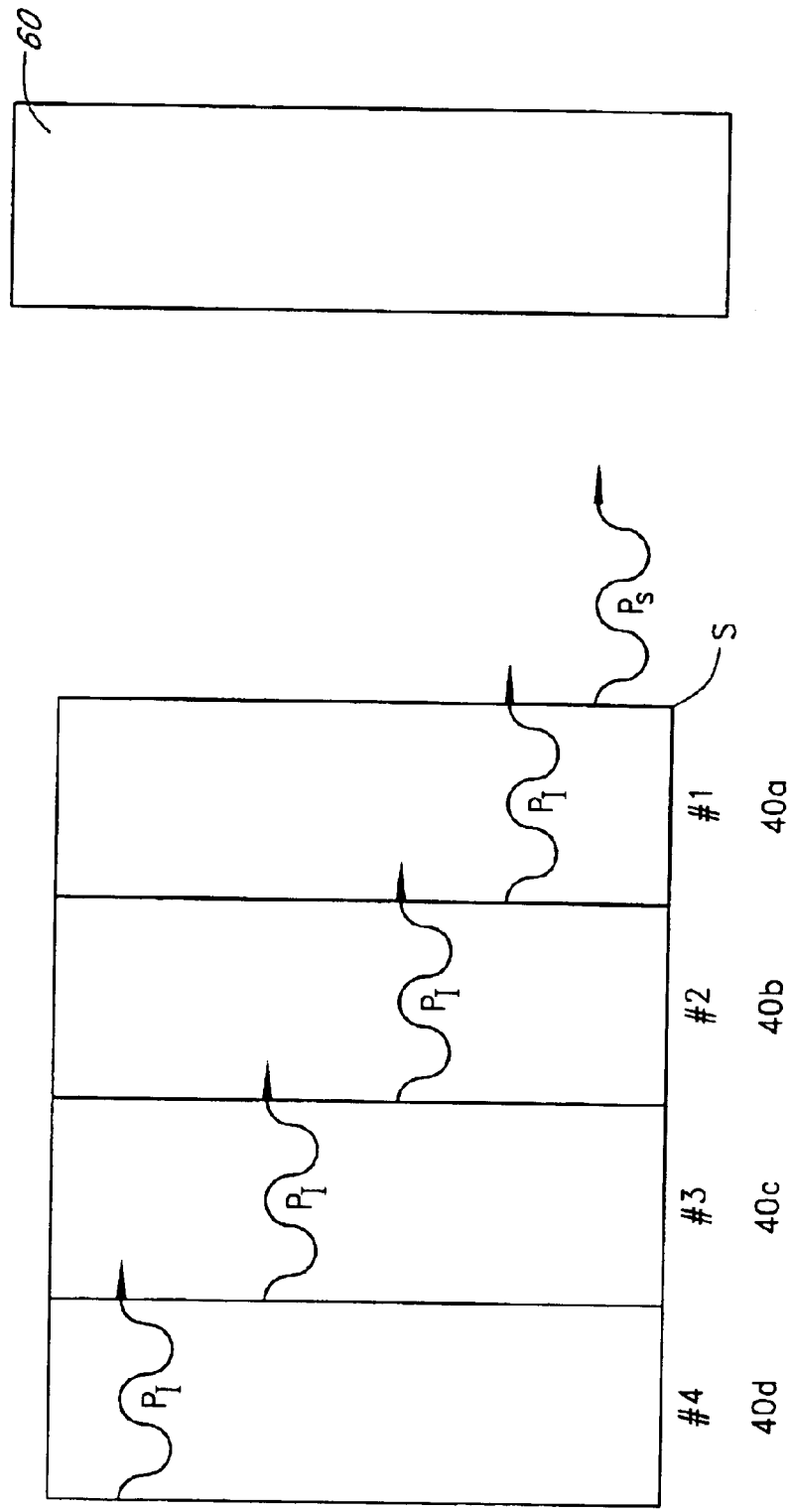
FIGS. 5 and 6 are the photon emission effects on cross-section views of a test sample in the presence and absence of a temperature gradient.
Figure 6:
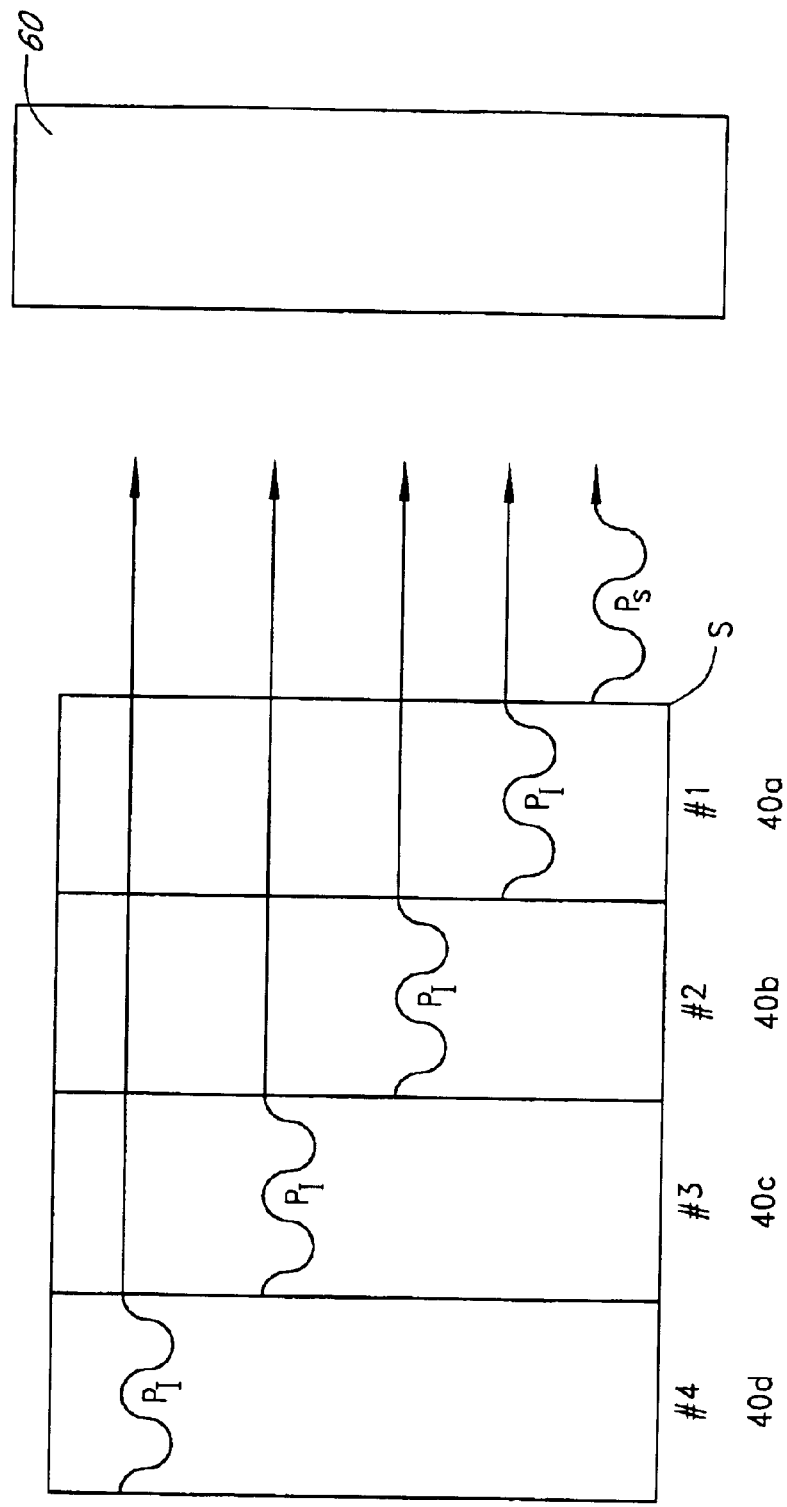

FIGS. 5 and 6 illustrate the transmission/absorbance aspect of the present invention. FIG. 5 is a cross-section view of a typical sample material 40 at an arbitrarily warm uniform temperature (e.g., about 37° C.) For illustrative purposes, the sample 40 of FIG. 5 is shown having a surface S and layers 40a, 40b, 40c, and 40d each representing successively deeper portions of the sample. Each layer being approximately 10 μm further inside the sample 40. Layer 40d being 30 μm beneath the sample surface S. Without a gradient, photons $P_d$ emitted within the sample are reabsorbed by the sample within a very short distance (approximately 10–20 μm). Only photons $P_S$ emitted at or near the surface S exit the sample to be detected by an external detector 60. The radiation emission spectra of these photons $P_S$ is determined by the temperature and emissivity em, of the sample 40.

FIG. 6 shows the effects of inducing a gradient in the sample 40 of FIG. 5. The surface S has been cooled (e.g. to about 10° C.) while a deeper layer 40d remains warm (e.g. 37° C.) with the intervening layers 40a, 40b, 40c, exhibiting gradually cooler temperatures as the 10° C. surface S is approached. As previously explained, in the presence of a gradient, the total radiation reaching the surface S, represented by photon $P_S$ and detected by the dector 60 is the sum of the radiation emitted by each of the layers 40a, 40b, 40c, and 40d, represented by photons $P_1$ weighted by the absorbance of the medium between each layer and the surface. Since a temperature gradient has been induced such that overlying layers are cooler than deeper layers the spectrum of radiation emitted from the surface will differ from the black body spectrum emitted by an object of uniform temperature. The absorbance of intervening layers through which emitted radiation, $P_1$, passes will alter the emitted spectrum in a manner that depends on the concentration of substances in the intervening layers.

Referring to FIG. 6, the internally emitted photons $P_1$ pass through intervening sample material 40a, 40b, 40c, and S. The intervening material 40a, 40b, 40c, and S absorbs some of the radiation reducing radiation output by the time it reaches the detector 60. The analytes in the intervening regions 40a, 40b, 40c, and S absorb radiation at specific characteristic wavelengths This reduces the radiation output at those wavelengths in a concentration-dependent manner. By comparing a detector signal at selected absorbance peak wavelengths with a reference signal at selected reference wavelengths, the analyte concentration may be determined.

Using this basic concept the present invention overcomes many of the practical impediments encountered in the prior art, including difficulties in resolving low analyte concentrations and tissue interference problems. The method of the present invention overcomes many of these difficulties by introducing a large temperature gradient in the sample to increase the detectable signal. Furthermore, by inducing a periodic temperature gradient in a sample substantial increases in accuracy and a much larger signal-to-noise ratio may be attained. The only limitations on gradient magnitude being the initial sample temperature and the necessity to avoid damaging the sample by making it too hot or too cold. These limitations become especially important when living tissue samples are used. Too high a temperature and the tissue burns, too cool and the tissue freezes. As a result preferable temperatures range from about 0° C. to about 40° C. for living test samples.

In its most basic embodiment the present invention provides a method for determining the concentration of chemical analytes in a test sample. The method is typically used in conjunction with a testing apparatus constructed for measuring analyte concentration. As shown in the block diagram of FIG. 7, such an apparatus 70 comprises a thermal gradient inducing means 62, a radiation detector 60, and a data processing means 64 for controlling the gradient and determining analyte concentration based on detector information and predetermined database. One satisfactory apparatus for implementing the method of the present invention is described in co-pending U.S. patent application Ser. No. 09/265,195.

In the analysis of test samples the tester typically knows what analytes he is seeking. The analyte sought is identified, and its IR absorbance spectrum analyzed. Analyte absorbance peaks are identified. Once one or more absorbance peak wavelengths are identified, one or more reference wavelengths are chosen. A temperature gradient is induced in the test sample. Subsequently, the sample radiation emissions are monitored with an IR detector. Detector signals are monitored. Signals are monitored at predefined wavelength intervals defined by absorbance characteristics of the analyte sought. These signals are referred to as analytical emission signals or just analytical signals. Typically, the analytical signals are measured at analyte absorbance peak wavelengths. IR detector signals are also monitored at so-called reference wavelengths. These are referred to as reference emission signals or just reference signals. It is advantageous to measure reference signals at wavelengths do not overlap the analyte absorbance peaks and it is advantageous if reference signals and analytical signals are not measured at wavelengths that overlap absorbance peaks of other possible constituents of the sample.

The reference wavelengths are typically dictated by the absorbance spectrum of the main constituent of the sample. Commonly, the main constituent is the medium in which the analytes are suspended. Frequently, especially in biological samples, the main constituent is water. Therefore, any analyte measurement must take into consideration the large amounts of water present. Reference measurements may be taken in regions where sample media absorbance is low (i.e., transmission near 100%). However, there are advantages to using reference measurements taken in regions where the sample media absorbance is high (i.e., transmission near 0%). Alternatively, reference measurements may be taken in regions bracketing the analyte absorbance peaks in question. Ideally, analyte absorbance peaks are chosen in regions where the absorbance effects of the major constituents are small. It is the way in which the information gathered at these absorbance and reference wavelengths is processed which allows the present invention to determine analyte concentration.

The present invention combines detector output measurements taken at the appropriate wavelengths with analysis of the radiation emission spectra of the subject material at known temperatures to facilitate the accurate determination of analyte concentration.

As previously discussed, most analytical samples exhibit blackbody or near blackbody radiative characteristics. This allows an accurate prediction of the expected radiation emission spectra based on temperature. Deviations from this expected spectra at selected wavelengths provide information used to determine analyte concentration.

A. Embodiment of the Present Invention Using a Non-Periodic Gradient

An application of the present invention is illustrated in the following noni-invasive determination of blood ethanol concentration in a human test subject.

Figure 9:
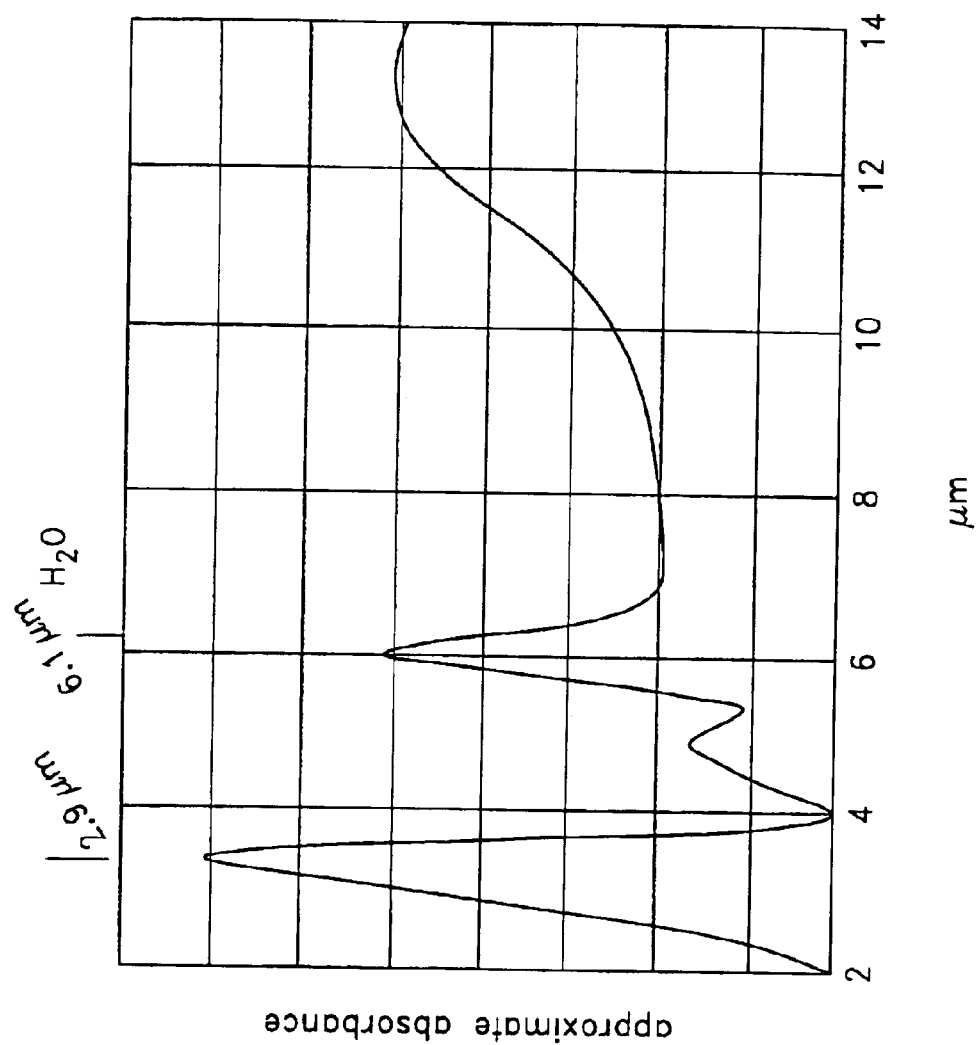
FIGS. 9, 10, and 11 show the absorbance spectra of water, ethanol, and glucose, respectively.
Figure 10:
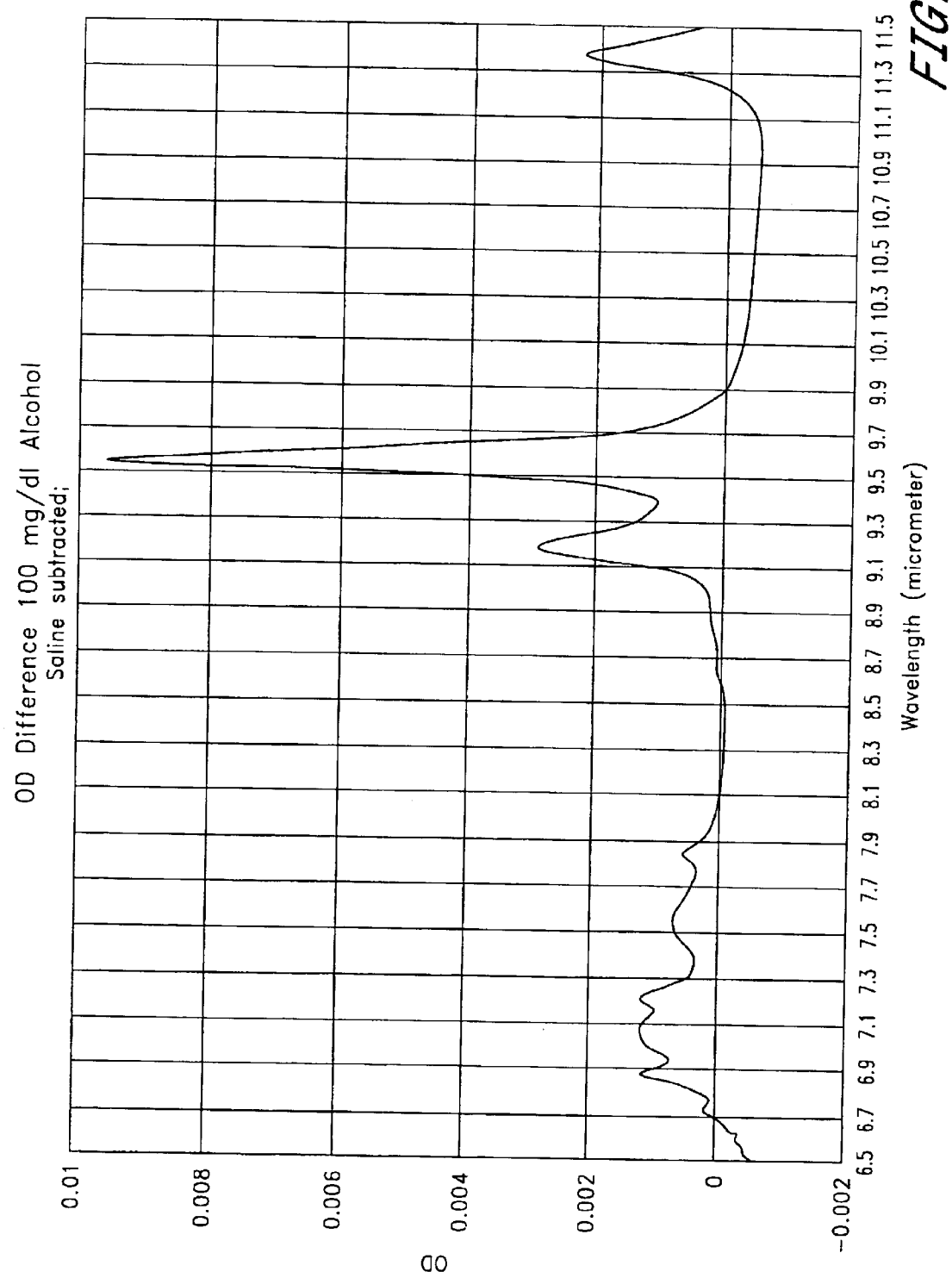

The major constituent of human blood is water. Blood is essentially a suspension of biological compounds in a water media. For the purpose of this illustration, the analyte of interest is ethanol. FIGS. 9 and 10 depict the IR spectra of water and ethanol, respectively. Referring to FIG. 9, water absorbance peaks are present at 2.9 $\mu$m and 6.1 $\mu$m. A transmittance peak exists in the range of about 3.6 $\mu$m to 4.2 $\mu$m. Additionally an area of relatively uniform absorbance exists between about 6.8 $\mu$m and about 11.0 $\mu$m. Referring to FIG. 10, ethanol absorbance peaks are shown between about 9.3 $\mu$m and 10.1 $\mu$m.

For the sake of illustration, we assume that the sample (blood and ethanol) has an emission spectrum similar to a blackbody radiator (FIG. 2). The blackbody radiative characteristics provide a source of known IR radiation which may be used to analyze the constituents of the sample.

Figure 7:
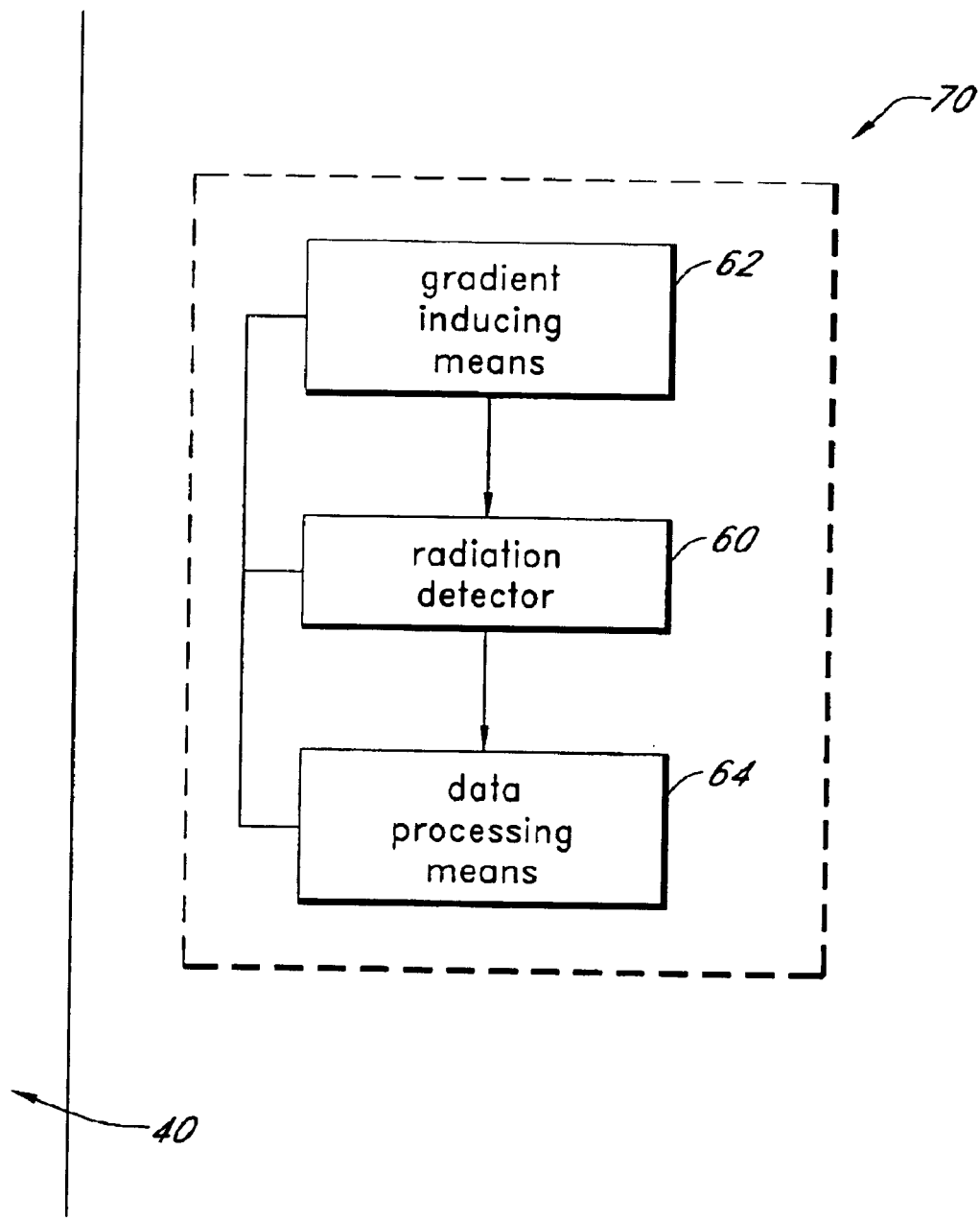
FIG. 7 is a block diagram showing a satisfactory apparatus for implementing the method of the present invention.
Figure 8:
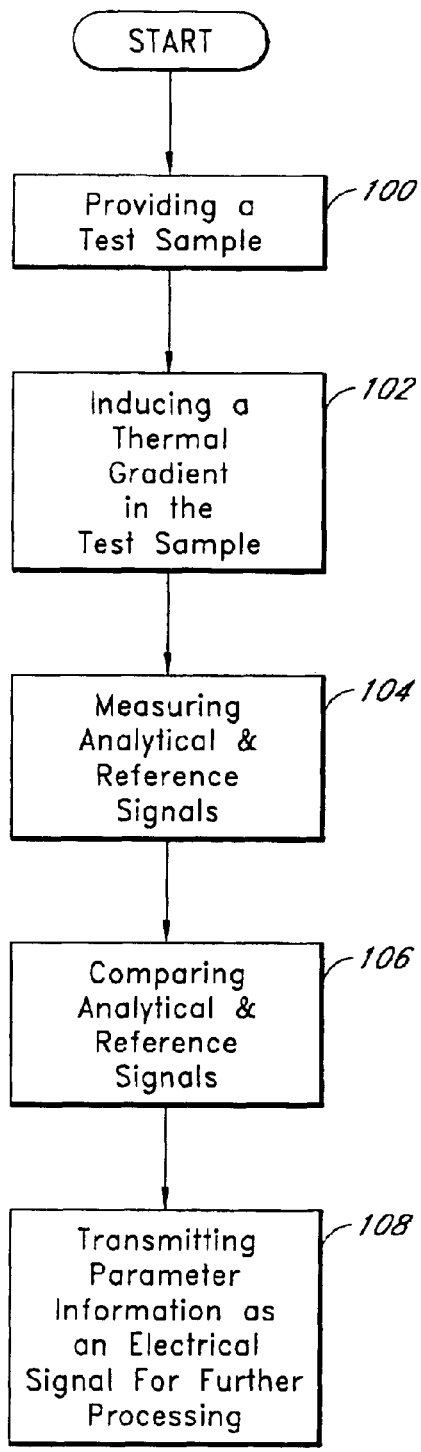
FIG. 8 is a flowchart showing an embodiment of the present invention.

Referring to FIGS. 7 and 8 an apparatus of FIG. 7 is employed according to the flowchart of FIG. 8. In Step 100 a test sample 40 is provided at some arbitrarily warm constant uniform initial temperature (e.g., approximately 37° C.), no gradient exists. In Step 102, a temperature gradient is induced in the sample 40 (for example, by subjecting the surface of the sample to a cooling event using means 62). Radiation passing through the gradient passes through the ethanol suspended in the sample and reaches the surface where it is detected by an IR detector 60. In Step 104 radiation is measured at selected wavelengths (specifically, at reference wavelengths and analyte absorbance peaks) producing analytical signals and reference signals. In Step 106 analytical signals and reference signals are compared and analyzed to determine phase differences caused by changes in the absorbance spectra in the affected regions. The present invention determines the analyte concentration in the sample by comparing the absorbance effects of the analyte with known absorbance information. This comparison and analysis is typically done using a data processing means 64. In Step 108, this concentration information is then transmitted, as an electrical signal, for further processing.

Figure 12:
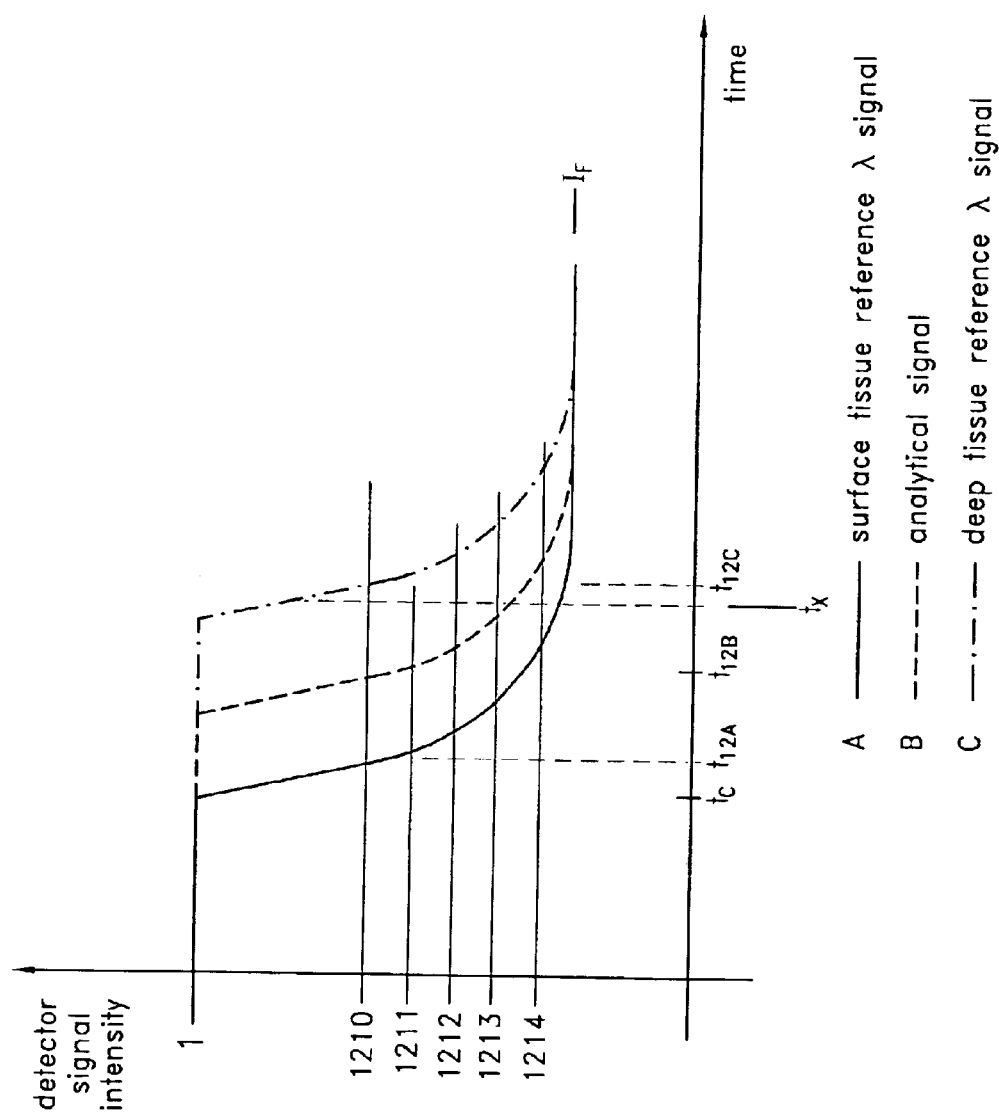
FIG. 12 is a graphical representation of the skin's response to a single induced temperature gradient with the y-axis representing detector signal intensity and the x-axis representing time.

Referring to FIGS. 8 and 12, in Step 104, a first reference signal 12A may be measured at a first reference wavelength. In the case of ethanol in a water media, a first reference signal is measured at a wavelength where water strongly absorbs (e.g., 2.9 $\mu$m or 6.1 $\mu$m as shown in FIG. 9). Because water strongly absorbs radiation at these wavelengths, the detector signal intensity is reduced at those wavelengths. Moreover, at these wavelengths water absorbs the photon emissions emanating from deep inside the sample. The net effect being that a signal emitted from deep inside the sample is not detected. The first reference signal 12A is a good indicator of gradient effects near the sample surface and is known as a surface reference signal. This signal may be calibrated and normalized to a value of 1. For greater accuracy, the detector signal at more than one first reference wavelength may be measured. For example, both 2.9 $\mu$m and 6.1 $\mu$m may be chosen as first reference wavelengths.

Still referring to FIG. 12, a second reference signal 12C may also be measured. The second signal 12C may be measured at a wavelength where water has very low absorbance (e.g., 3.81 $\mu$m or 5.5 $\mu$m as shown in FIG. 7). Unlike the first reference signal 12A, the second reference signal 12C is measured at a wavelength largely transparent to radiation. This signal may also be calibrated and normalized to a value of 1. This second reference signal 12C provides the analyst with information concerning the deeper regions of the sample, whereas the first signal 12A provides information concerning the sample surface. As with the first (surface) reference signal 12A, greater accuracy may be obtained by using more than one second (deep) reference signal 12C.

In order to determine analyte concentration, a third signal 12B is also measured. This signal is measured at an IR absorbance peak of the selected analyte. Ethanol peak wavelengths are in the range of about 9.3–10.1 $\mu$m (as shown in FIG. 9). This detector signal may also be calibrated and normalized to 1. As with the reference signals 12A, 12C, the analytical signal 12B may be measured using more than one absorbance peak.

Optionally, or additionally, reference signals may be measured at wavelengths that bracket the analyte absorbance peak. Using the ethanol example, bracketing wavelengths may be chosen at 7.0–8.0 $\mu$m and 10.3–11.5 $\mu$m. These signals may also be calibrated and normalized to a value of 1. These signals may be advantageously monitored at reference wavelengths which do not overlap the analyte absorbance peaks. Further, it is advantageous to measure reference wavelengths and absorbance peaks which do not overlap the absorbance peaks of other possible constituents contained in the tissue. Corrections for known extraneous biological matter contained in a sample may be made if desired.

In Step 106, the analytical 12B and reference, signals 12A, 12C are compared. Referring to FIG. 12, the signal intensities 12A, 12B, 12C all begin at an initial signal intensity (all shown here at a normalized value of 1). This reflects the baseline radiation behavior of a test sample in the absence of a gradient. In Step 102, at some time, $t_C$, the surface of the sample is subjected to a temperature event which induces a temperature gradient in the sample surface. This gradient can be induced by heating or cooling the sample surface. The example shown in FIG. 12 uses cooling, for example, using a 10° C. cooling event. Similar to FIG. 3, the detector signal decreases over time. However, due to the effects of the temperature gradient and variances in absorbance, each signal 12A, 12B, 12C decreases in intensity.

Since the cooling of the sample is neither uniform nor instantaneous, the surface cools before the deeper regions of the sample cool. As each of the signals 12A, 12B, 12C are monitored as they drop in intensity, a pattern emerges. Signal intensity declines as expected, but if the signals are monitored as they reach a set amplitude value (or series of amplitude values: 1210, 1211, 1212, 1213, 1214), certain temporal effects are noted. After the cooling event is induced at $t_c$, the first (surface) reference signal 12A declines in amplitude most rapidly, reaching a checkpoint 1210 first, at time $t_{l2A}$. This is due to the fact that the first reference signal 12A mirrors the sample's radiative characteristics near the surface of the sample. Since the sample surface cools before the underlying regions, the surface (first) reference signal 12A drops in signal intensity first.

Simultaneously, the second reference signal 12C is monitored. Since the second reference signal 12C mirrors the radiation characteristics of deeper regions inside the sample, which do not cool as rapidly as the surface (due to the time needed for the surface cooling to propagate into the deeper regions of the sample), the intensity of signal 12C does not decline until slightly later. Consequently, signal 12C does not reach magnitude 1210 until some later time $t_{12C}$. This results in a time delay between the time $t_{12A}$ that the amplitude of the first reference signal 12A reaches the checkpoint 1210 and the time $t_{12C}$ that the second reference signal 12C reaches the same checkpoint 1210. This time delay can be expressed as a phase difference $\Phi(\lambda)$. Additionally, a phase difference may be measured between the analytical signal 12B and either or both reference signal 12A, 12C. These phase differences $\Phi(\lambda)$ are compared in Step 106 of FIG. 8. As the concentration of analyte increases, the amount of absorbance at the analytical wavelength increases. This reduces the intensity of the analytical signal 12B in a concentration dependent way. Consequently, the analytical signal 12B reaches intensity 1210 at some intermediate time $t_{12B}$. The higher the concentration of analyte, the more the analytical signal 12B shifts to the left. As a result, with increasing analyte concentration, the phase difference $\Phi(\lambda)$ relative to the first reference signal 12A decreases and relative to the second reference signal 12C (the deep tissue signal) the phase difference $\Phi(\lambda)$ increases. These phase differences $\Phi(\lambda)$ are directly related to analyte concentration and can be used to make accurate determinations of analyte concentration.

Phase difference $\Phi(\lambda)$ between the surface reference signal 12A and the analytical signal 12B is represented by the equation:

$$\Phi(\lambda)=t_{12A}-t_{12B}$$

The magnitude of this phase difference decreases with increasing analyte concentration.

Whereas, the difference $\Phi(\lambda)$ between the deep 12C and analytical 12B signals is represented by the equation:

$$\Phi(\lambda)=t_{12B}-t_{12C}$$

The magnitude of this phase difference increases with increasing analyte concentration.

Accuracy may be enhanced by choosing several checkpoints, for example, 1210, 1211, 1212, 1213, and 1214 and averaging the phase difference $\Phi(\lambda)$. The accuracy of this method may be further enhanced by integrating the phase difference $\Phi(\lambda)$ continuously over the entire test period. Because only a single temperature event has been induced and because measurements must be taken only in the presence of a temperature gradient all measurements must be taken before a new lower equilibrium temperature is reached and the signals stabilize at a new constant level $I_F$ and the gradient vanishes. Further accuracy may be obtained by measuring detector signals at reference wavelengths chosen near analyte absorbance peaks. The point should be made that the method works equally well with temperature gradients induced by heating.

Furthermore, the method of the present invention is not limited to the determination of phase difference $\Phi(\lambda)$. At any given time (for example, at time $t_x$) the amplitude of the analytical signal 12B may be compared to the amplitude of either or both of the reference signals 12A, 12C, The difference in signal magnitude may be correlated and processed to determine analyte concentration. Also, the analytical signal 12B and the reference signals 12A, 12C may be processed for concentration dependent frequency information. The differences in each of these parameters (phase, magnitude, and frequency) may be processed using the data processing means of the present invention (not shown) to determine analyte concentration.

The invention is versatile. This method is not limited to the detection or quantification of in-vitro ethanol concentration. As stated previously, the method may be used on human, animal, or even plant subjects. The method may be used to take non-invasive measurements of in-vivo samples of virtually any kind. In addition to blood samples, the method is adaptable and may be used to determine chemical concentrations in other body fluids (e.g., urine or saliva) once they have been extracted from a patient. In fact, the method may be used for the measurement of in-vitro samples of virtually any kind. The method is useful for measuring the concentration of a wide range of additional chemical analytes, including but not limited to, glucose, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, hormones, as well as other chemical compounds. All that is required is the careful selection of analytical and reference wavelengths.

B. Embodiment of the Present Invention Using Periodically Modulated Temperature Gradients.

The principles of the present invention may be applied to a more elegant method of determining analyte concentration. By using a periodically modulated temperature gradient, a more accurate determination of analyte concentration may be made.

Figure 13:
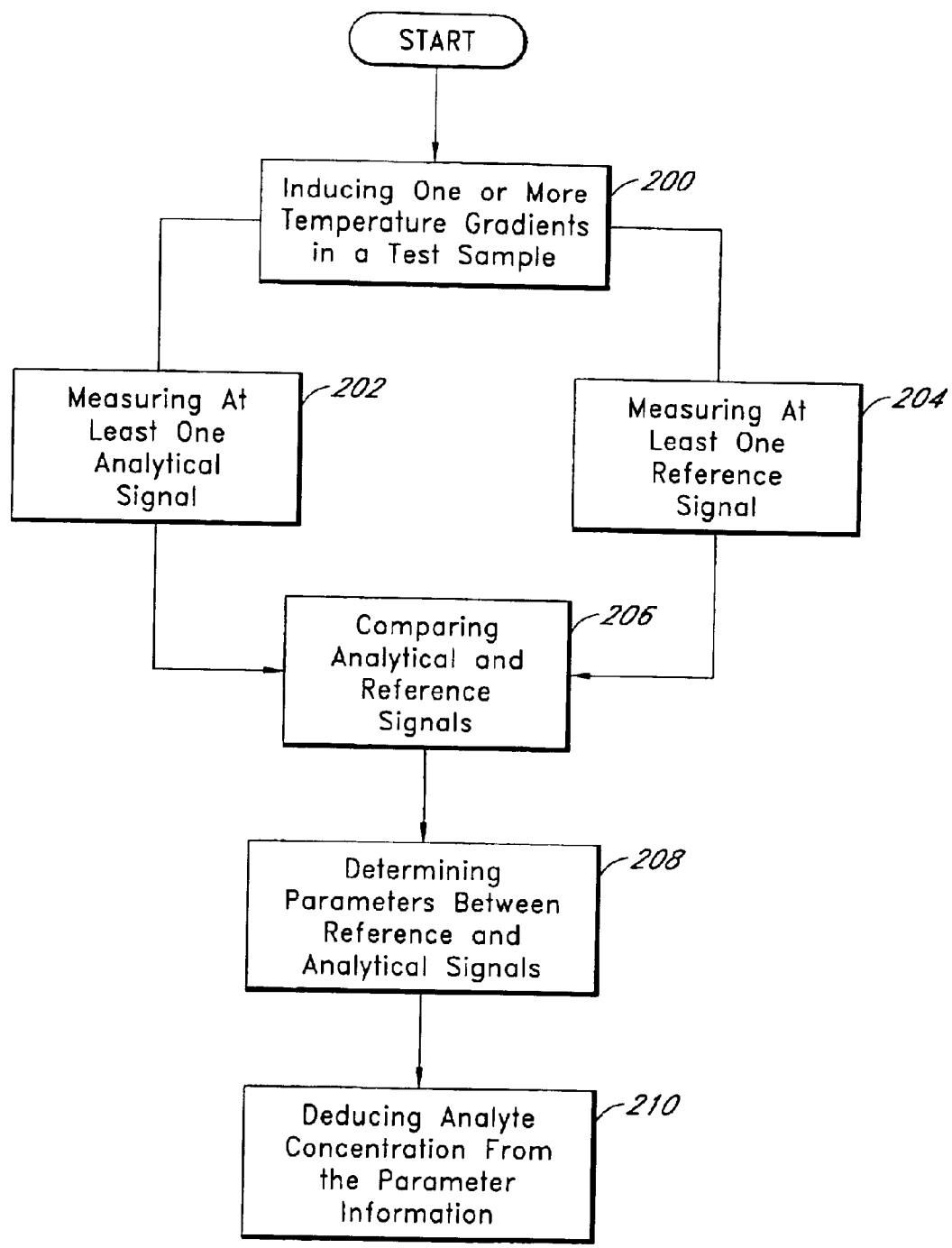
FIG. 13 is a flowchart showing a second embodiment of the present invention.

FIG. 13 is a flowchart of an embodiment of the present invention using a periodically modulated temperature gradient to determine the analyte concentration of a sample. In Step 200, a periodic gradient is induced in a sample. In Steps 202 and 204, the radiation output of the sample is measured using at least one analytical signal and at least one reference signal. In Step 206 the analytical and reference signals are compared and processed. Subsequently, in Step 208, the processed information is used to determine parameter differences between said analytical and reference signals. In Step 210, the parameter signal is used in conjunction with predetermined parameter information to deduce the analyte concentration of the sample.

Figure 11:
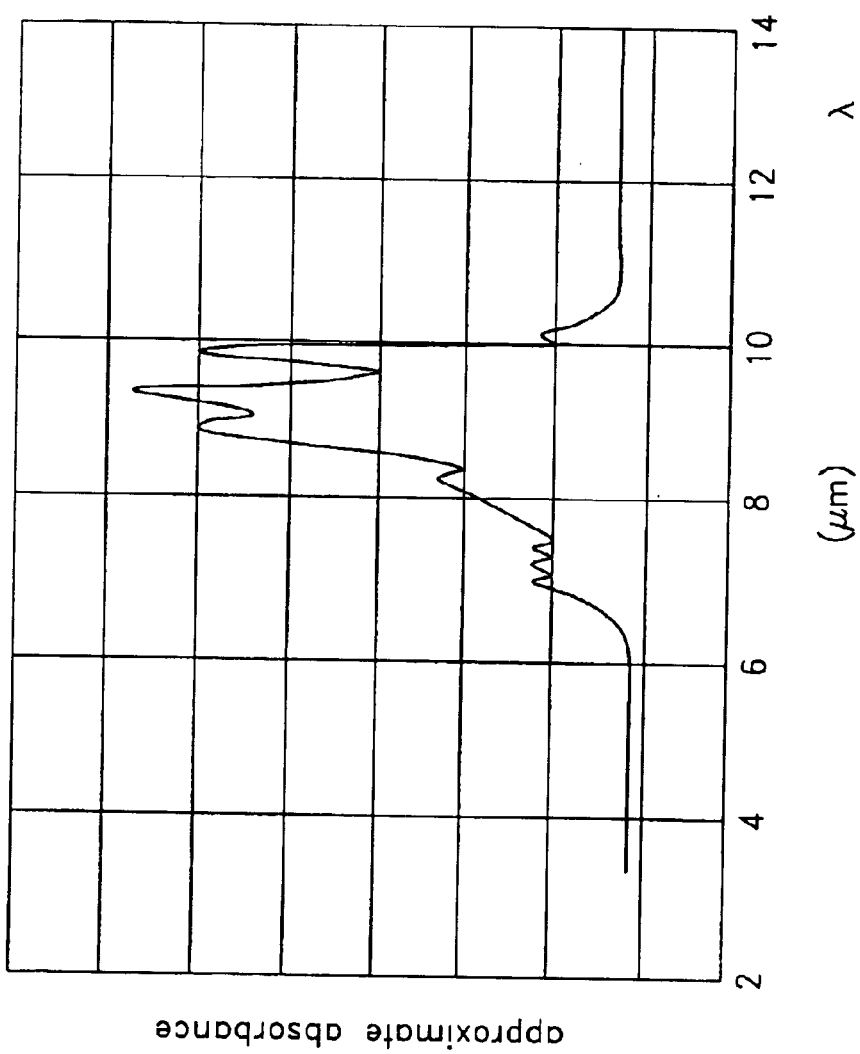

The following example illustrates a determination of blood glucose concentration in a test sample The parameter chosen in this example is phase difference. Alternatively, the parameter may be frequency or amplitude. FIGS. 9 and 11 depict the IR spectra of water and glucose, respectively. Referring to FIG. 9, water absorbance peaks are present at 2.9 $\mu$m and 6.1 $\mu$m. A transmittance peak exists in the range of about 3.6 $\mu$m to 4.2 $\mu$m. Additionally, an area of relatively uniform absorbance exists between about 6.8 $\mu$m and about 11.0 $\mu$m. Referring to FIG. 11, a number of glucose absorbance peaks exist between about 6.5 $\mu$m and 11.0 $\mu$m.

As previously shown, in FIG. 12, once a gradient is induced, the reference and analytical signals 12A, 12B, 12C are out of phase with respect to each other. This phase difference $\Phi(\lambda)$ is present whether the gradient is induced through heating or cooling. This feature of the invention has tremendous advantages. The present invention advantageously exploits the fact that phase difference $\Phi(\lambda)$ exists in the presence of both positive and negative gradients. By alternatively subjecting the test sample to cyclic pattern of heating then cooling, a continuous gradient may be induced in a sample for an extended period of time.

Figure 14:
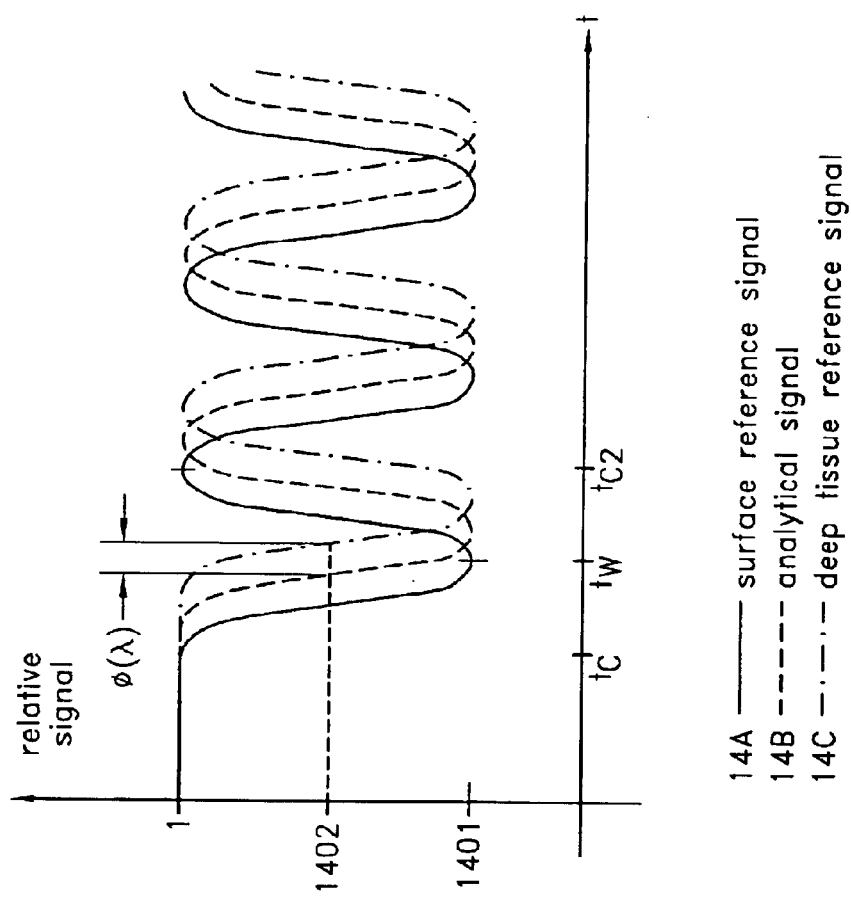
FIG. 14 is a graphical representation of skin response to a periodically modulated temperature gradient with the y-axis representing detector signal intensity and the x-axis representing time.

The principle of a continuous gradient is illustrated using a simple sinusoidally modulated temperature gradient. FIG. 14 graphically depicts detector signals emanating from a test sample. As with the previously disclosed embodiment shown in FIG. 12, one or more reference signals 14A, 14C are measured. One or more analytical signals 14B are also monitored. These signals may optionally be normalized to a value of 1. FIG. 14 shows the signals after normalization. At some time $t_c$, a temperature event (e.g., cooling) is induced at the sample surface. This causes a decline in detector signal. As shown in FIG. 12, the signals (12A, 12B, 12C) decline until the gradient disappears and a new equilibrium detector signal $I_F$ is reached. In the present embodiment (FIG. 14), as the gradient begins to disappear at signal intensity 1401 a heating event, at time $t_w$, is induced in the sample surface. As a result the detector output signals 14A, 14B, 14C will rise as the sample temperature rises. At some later time $t_{c2}$, another cooling event is induced, causing the temperature and detector signals to decline. This cycle of cooling and heating may be repeated over an arbitrarily long time interval. Moreover, if the cooling and rewarming events are timed properly, a periodically modulated temperature gradient may be induced in the test sample. Such a periodic gradient is the objective of Step 200 of FIG. 13.

As previously explained in the discussions relating to FIG. 12, a phase difference $\Phi(\lambda)$ may be measured and used to determine analyte concentration. In the present embodiment, periodic reference (14A, 14C) and analytical 14B signals are measured in Steps 202 and 204. The reference (14A, 14C) and analytical 14B wavelengths are chosen for analysis based on the same considerations used to determine the reference and analytical wavelengths shown in FIG. 12 (i.e., absorbance peaks, transmission peaks, non-interference with the media). FIG. 14 shows these signals after an optional normalization step has occurred.

FIG. 14 shows that a first (surface) reference signal 14A declines and rises in intensity first. A second (deep tissue) reference signal 14C declines and rises in a time-delayed manner relative to the first reference signal 14A. The analytical signal 14B exhibits a time delay dependent on the analyte concentration. With increasing concentration, the analytical signal 14B shifts to the left. As with FIG. 12 a phase difference $\Phi(\lambda)$ may be measured.

In Steps 206 and 208, reference signals 14A, 14C are compared with analytical signals 14B to determine a phase difference $\Phi(\lambda)$. For example, a phase difference $\Phi(\lambda)$ between the second reference signal 14C and an analytical signal 14B, measured at some set amplitude 1402 is shown. The phase difference $\Phi(\lambda)$ can be used to determine the phase difference between any reference signal 14A, 14C and any analytical signal 14B to generate a phase signal as in Step 208. The magnitude of the phase signal reflects the analyte concentration of the sample. In Step 210 the phase difference $\Phi(\lambda)$ information is correlated by the data processing means 64 with previously determined phase information (typically stored in the data processing means 64 of FIG. 7) to determine the analyte concentration in the sample.

A further advantage of the present method is that the phase difference $\Phi(\lambda)$ is constant and continuous measurements of phase may be integrated over the entire test period for an extremely accurate measure of phase difference $\Phi(\lambda)$. By inducing and maintaining a temperature gradient and integrating continuous measurements of phase difference $\Phi(\lambda)$ throughout an entire test period, the signal-to-noise ratio may be substantially increased resulting in very accurate determinations of phase. Further, the accuracy of the method may be improved by using more than one reference signal and/or more than one analytical signal.

Additionally, the present method may be advantageously employed to simultaneously measure the concentration of one or more analytes. By choosing reference and analyte wavelengths that do note overlap, phase differences can be simultaneously measured and processed to determine analyte concentrations.

Although FIG. 14 illustrates the method used in conjunction with a sinusoidally modulated temperature gradient, the principle applies to temperature gradients conforming to any periodic function. In such more complex cases, analysis using signal processing with Fourier transforms or other techniques allows accurate determinations of phase difference $\Phi(\lambda)$ and analyte concentration. Such processing may be accomplished using the data processing means 64 of FIG. 7.

C. Embodiment of the Present Invention Using Periodic Monitoring of Phase Signal.

Figure 15:
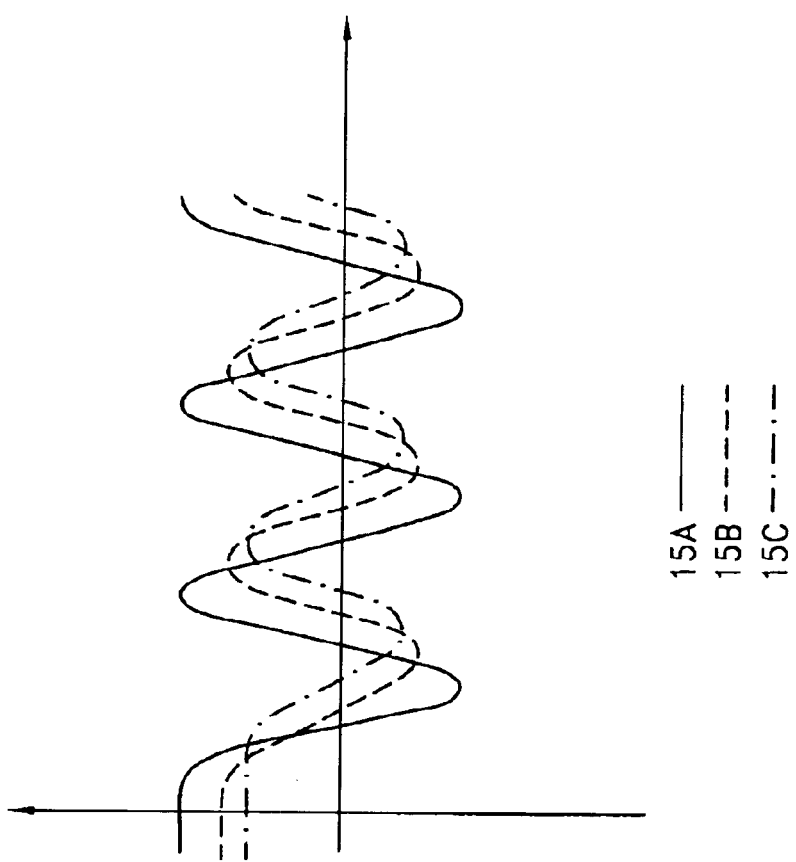
FIG. 15 is a graphical representation of skin response to a periodically modulated temperature gradient with the y-axis representing unnormalized detector signal intensity and the x-axis representing time.

Referring to FIG. 15, further advantages of the present invention include the ability to accurately determine analyte concentration using non-continuous measurements of phase. For example, the magnitude of the phase differences $\Phi(\lambda)$ may be determined by measuring the time intervals between the amplitude peaks (or troughs) of the reference signals 15A, 15C and the analytical signals 15B. Alternatively, the time intervals between the "zero crossings" (the point at which the signal amplitude changes from positive to negative, or negative to positive) may be used to determine the phase difference $\Phi(\lambda)$ between analytical signals 15B and the reference signals 15A, 15C. This information is subsequently processed and a determination of analyte concentration may then be made. The method has the advantage of not requiring normalized signals.

D. Embodiment of the Present Invention Using Periodic Gradients Induced at More Than One Driving Frequency.

Additionally, this application of the principles of the invention allows non-invasive quantification of analyte concentration in test samples comprised of heterogeneous material, such as complex biological tissues. A typical example being human skin.

Figure 16:
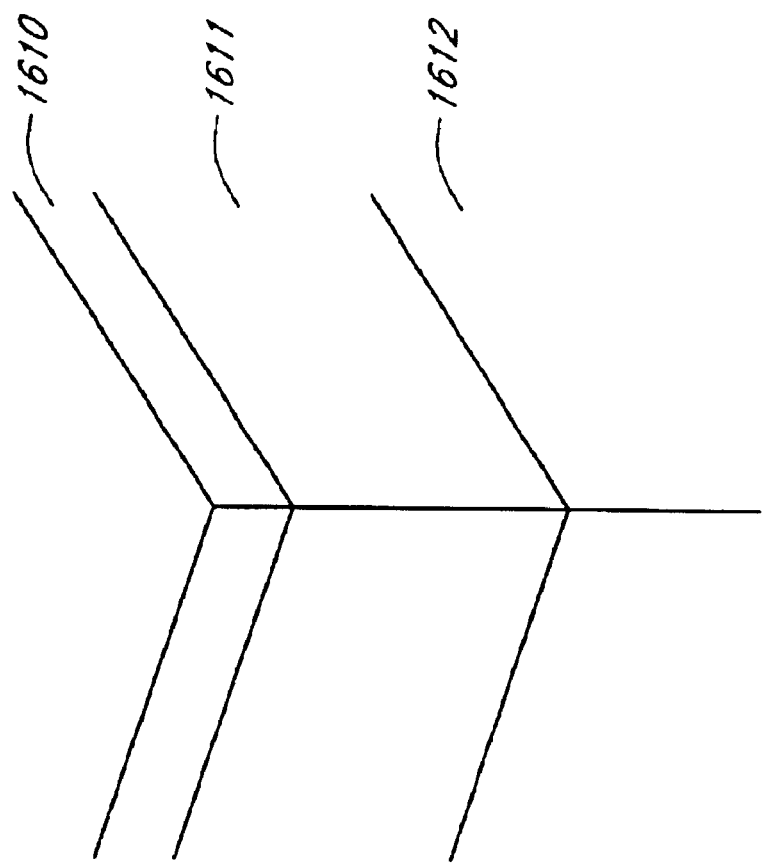
FIG. 16 is a schematic illustration of the human skin.

The skin's structure differs from the completely uniform homogeneous examples previously described. As shown in FIG. 16, skill is a layered structure. A thin layer of stratum corneum approximately 10 $\mu$m thick 1610 covers the surface of the skin, and contains no fluid. Underlying the stratum corneum is a layer of epidermis 1611 approximately 100$\mu$m thick. The epidermis 1611 contains fluids (e.g. interstitial and intracellular fluids) which are important because the fluids suspend analyte materials of interest (such as glucose). Beneath the epidermis 1611 lies a thick layer of derma 1612, which also contains fluid and suspended blood analytes (for example, glucose). It is the methods for analyzing these suspended analytes that form the present embodiment of the invention.

The human body's spectral radiation characteristics are very similar to that of the previously discussed blackbody radiator (FIG. 2). The near blackbody radiative characteristics of the human body provide a source of known IR radiation, which may be used to analyze the constituents of human blood contained within the skin.

Ordinarily, the body's internal temperature $T_1$ is constant at approximately 37° C. At ordinary room temperature (e.g., 21° C.), a naturally occurring temperature gradient exists in the skin. A 21° C. room temperature is less than the body's 37° C. internal temperature $T_1$. This causes a reduction of the skin's surface temperature $T_S$ to approximately 33° C. As a consequence, a small 4° C. temperature gradient exists between the body's 37° C. internal regions and the skin's 33° C. surface. Unfortunately, this naturally occurring gradient is not sufficient and a larger gradient is needed. The larger gradient equates to a greater detector signal and a better picture of thermal behavior deeper inside the skin. The present invention utilizes this phenomenon to analyze the body's chemical composition.

The present invention integrates all the previous concepts in a method of determining analyte concentration in heterogeneous (non-uniform) test samples. Specifically, the method of the present invention may be used to non-invasively determine the blood glucose concentration in human subjects. It allows the measurement of specific regions inside a test sample. This has significant advantages when used to analyze samples having non-uniform analyte distribution characteristics. This method finds particular utility in the non invasive analysis of biological tissues.

It will be recalled from the discussions concerning FIGS. 4(I)(a) through 4(IV)(b) that the temperature gradient penetrates into a test sample on a time-dependent basis (i.e., the longer the surface temperature event was present, the deeper the gradient penetrated into the sample). It is also recalled that photons emitted from areas beneath the gradient are reabsorbed within 10–20 $\mu$m of their point of origin, meaning that photons emanating from beneath the gradient do not reach the surface and are not detected. This allows the present invention to examine "slices" of a test sample at various depths.

Figure 17:
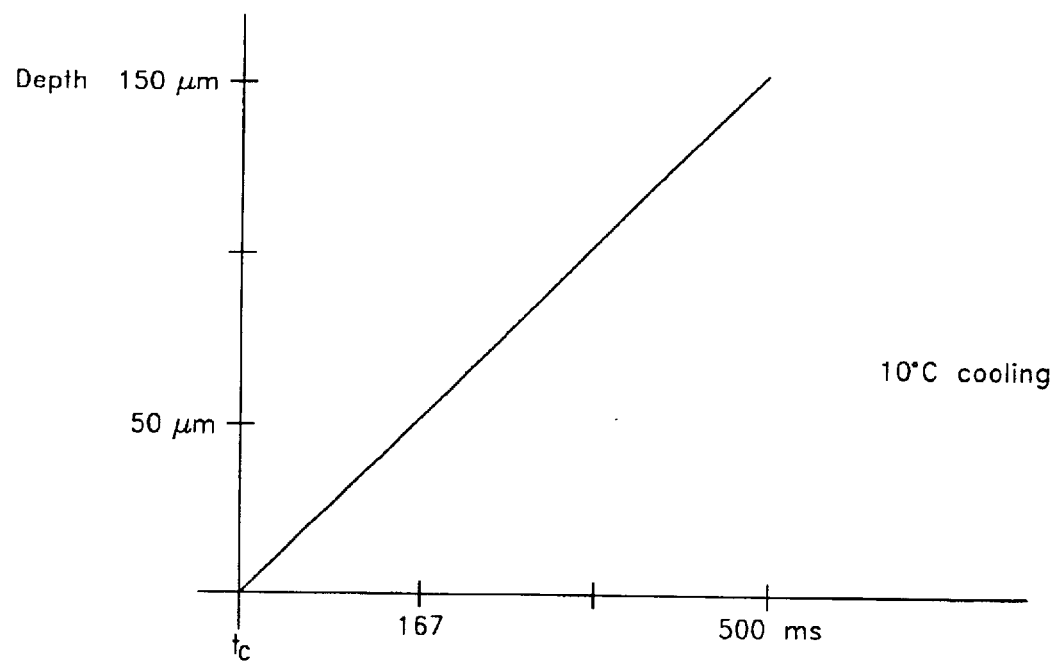
FIG. 17 is a graphical representation of skin response to a periodically modulated temperature gradient with the y-axis representing the depth to which the gradient penetrates and the x-axis representing the time that the skin has been exposed to a 10° C. cooling source.
Figure 18:
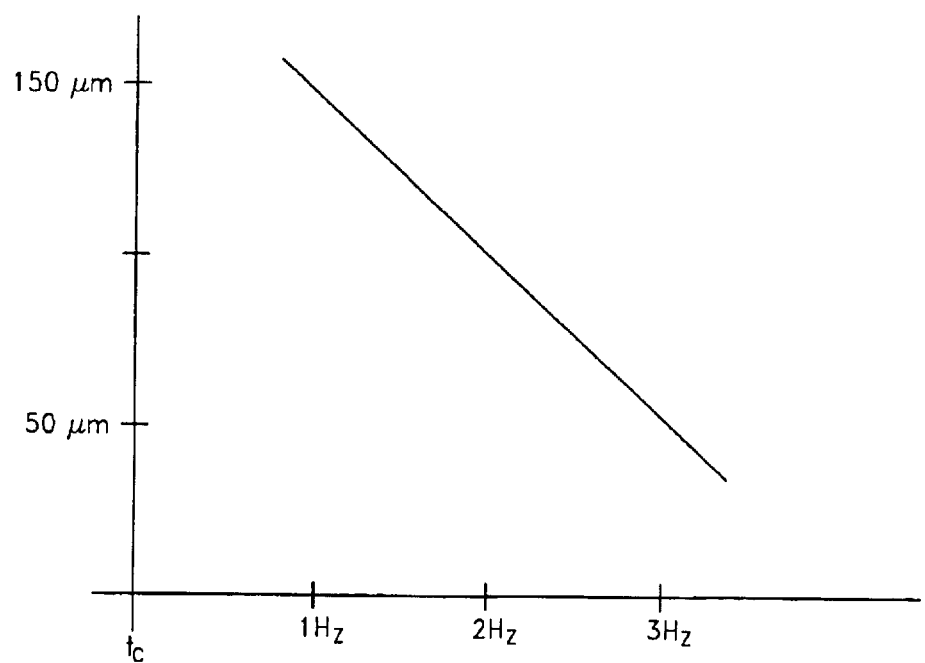
FIG. 18 is a graphical representation of skin response to a periodically modulated temperature gradient with the y-axis representing the depth to which the gradient penetrates and the x-axis representing the frequency of a gradient cooling/heating cycle.

FIGS. 17 and 18 illustrate this principle. FIG. 17 plots length of a temperature event versus depth of gradient. FIG. 18 plots frequency of a periodic cooling/heating cycle versus depth of gradient. Referring to FIG. 3, initially a test sample is at some arbitrarily warm constant temperature (e.g., 37° C.) when at some later time $t_c$, a cold event (e.g., 10° C.) is induced in the test sample. As expected, the detector signal 31 drops off as the sample cools. The limitations of the cooling/heating cycle are dictated largely by the limitations of the test sample. In the case of living human tissue, a cooling temperature of less than about 0° C. begins to freeze the tissue and a heating temperature of greater than about 40° C. begins to cause discomfort to the patient. This defines the limits of the heating and cooling cycle used for human subjects.

Referring to FIG. 17, for a human subject, using a temperature event of 10° C., after about 500 ms (milliseconds), the gradient penetrates to about 150 $\mu$m into the skin. Consequently, referring to FIG. 18, a cooling/heating cycle (also referred to as a driving frequency) of 1 Hz provides information to a depth of about 150 $\mu$m. It has also been determined that exposure to a 10° C. cooling event for about 167 ms leads to a gradient that penetrates to a depth of 50 $\mu$m (FIG. 17). Therefore, a cooling/heating cycle of 3 Hz provides information to a depth of about 50 $\mu$m (FIG. 18). By subtracting the detector signal information measured at a 3 Hz driving frequency from the detector signal information measured at a 1 Hz driving frequency, a picture of skin between 50 and 150 $\mu$m emerges.

This concept has particular usefulness when used to make non-invasive measurements of non-uniform or layered samples such as living tissue. The present invention uses a first (fast) driving frequency to induce a shallow temperature gradient and a second (slow) driving frequency to induce deeper gradients. The individual requirements for driving frequencies are determined by test sample and temperatures of the heating and cooling events. The phase information measured at each driving frequency is correlated and processed by a data processing means to accurately determine the analyte concentration.

In human skin the stratum corneum 1610 is 10–30 $\mu$m thick and provides little useful information concerning the concentration of blood analytes. However, the underlying derma 1611 and epidermis 1612 contain fluids which contain significant amounts of analytes. The present invention provides a method for determining analyte concentration in the underlying layers 1611, 1612 while compensating for the inaccuracies induced by the overlying stratum corneum 1610.

Figure 19:
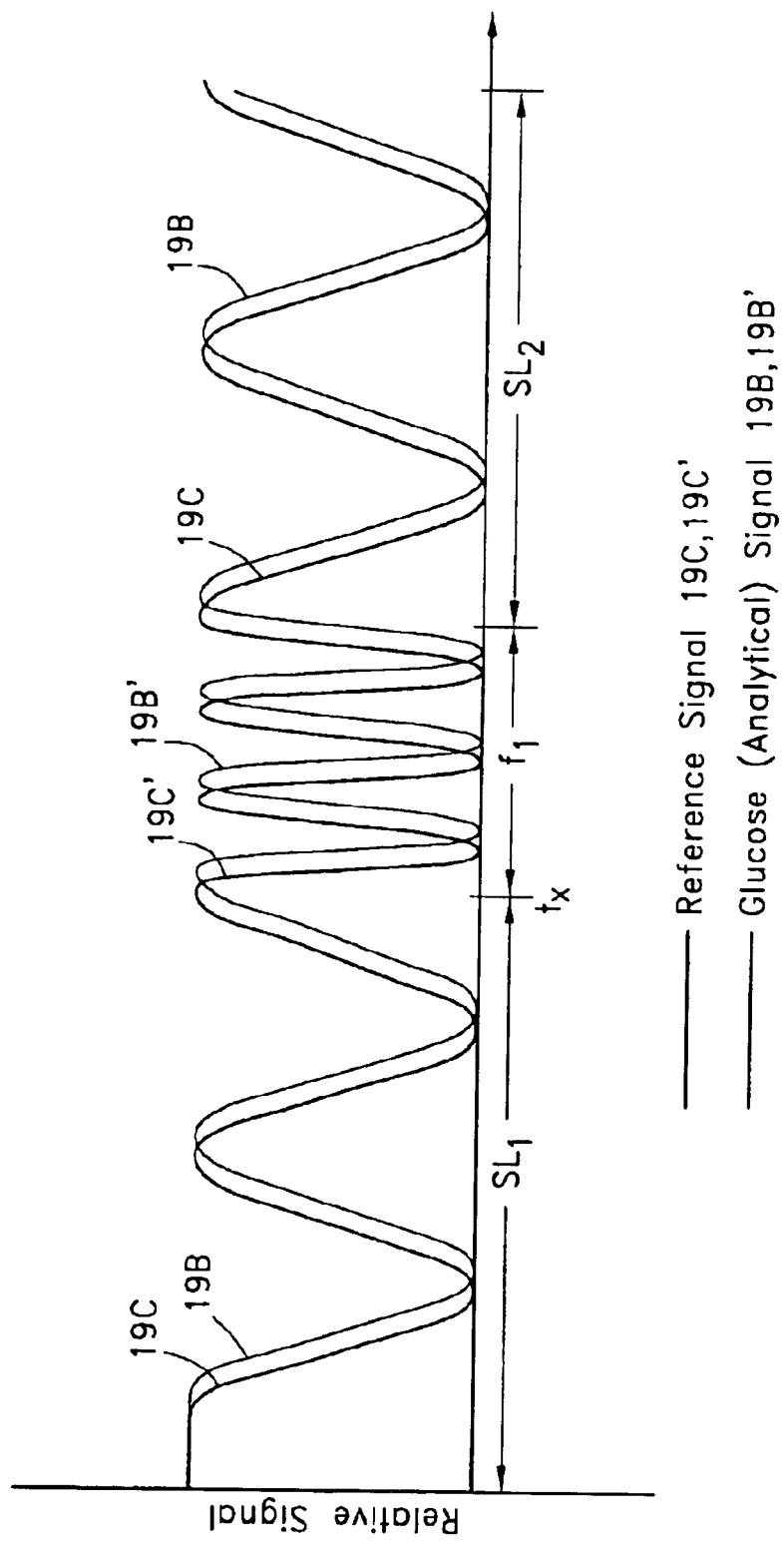
FIG. 19 is a graphical representation of skin response to a two sequential periodically modulated temperature gradients with the y-axis representing relative detector signal intensity and the x-axis representing the time or phase angle.

The present invention relies on the introduction of two sequentially implemented gradients. Each gradient having a different driving frequency. This embodiment also relies on the detection and measurement of phase differences $\Phi(\lambda)$ between reference 19C, 19C' and analytical 19B, 19B' signals. The present invention measures the phase differences $\Phi(\lambda)$ at both fast (e.g., 3 Hz) and slow (e.g., 1 Hz) driving frequencies. Referring to FIG. 19, a slow cycle (e.g., 1 Hz) provides measurements of analyte concentration in the region from 0 to about 150 $\mu$m. An analytical signal 19B is measured and a reference signal 19C is measured. A phase delay $\Phi(\lambda)$ is measured. The phase delay between 19B and 19C (this is similar to the phase delay between the analytical signal 14B and the deep tissue reference signal 14C of FIG. 14) is relatively longer at higher analyte concentrations. The slow driving frequency continues for arbitrarily chosen number of cycles (in region $SL_t$), for example, two full cycles. Then a higher driving frequency (fast cycle) temperature modulation is induced. Due to the higher frequency of the fast cycle (e.g., 3 Hz), only information contained in the shallower regions (e.g., the regions from 0–50 μm) of the skin is measured. An analytical signal 19B' is measured and a reference signal 19C' is measured at the higher driving frequency and the phase delay $\Phi(\lambda)'$ is determined. Since the shallower regions (i.e., the stratum corneum, 10–30 μm thick) have a lower analyte concentration, the phase delay is relatively smaller $\Phi(\lambda)'$. The fast cycle is also run through a number of cycles (for example, in region $f_1$, e.g., two cycles). By running through the fast and slow cycles a few times, the various phase delays $\Phi(\lambda)$, $\Phi(\lambda)'$ can be integrated over time. In fact, the pattern may be continued for any amount of time. The fast cycle (shallow tissue) phase data $\Phi(\lambda)'$ is subtracted from the slow cycle data $\Phi(\lambda)$, providing an accurate determination of analyte concentration in the region between 50 to 150 μm in depth.

According to another embodiment of the invention, instead of providing a driving frequency that changes sequentially from a high frequency to a low frequency, the two frequencies can be superposed so that high and low frequency signals are applied simultaneously. This embodiment has the advantage that signals from both near-surface and deeper layers are obtained at the same time, thereby reducing the total amount of time necessary to take a measurement in two layers of tissue. It should be noted, however, that where frequencies are imposed simultaneously, the total power at each frequency must be reduced so that the total power applied to a patient's tissues does not cause injury. Thus, the sequentially applied driving frequencies show in FIG. 19 can safely deliver greater power at each of the driving frequencies.

Figure 20:
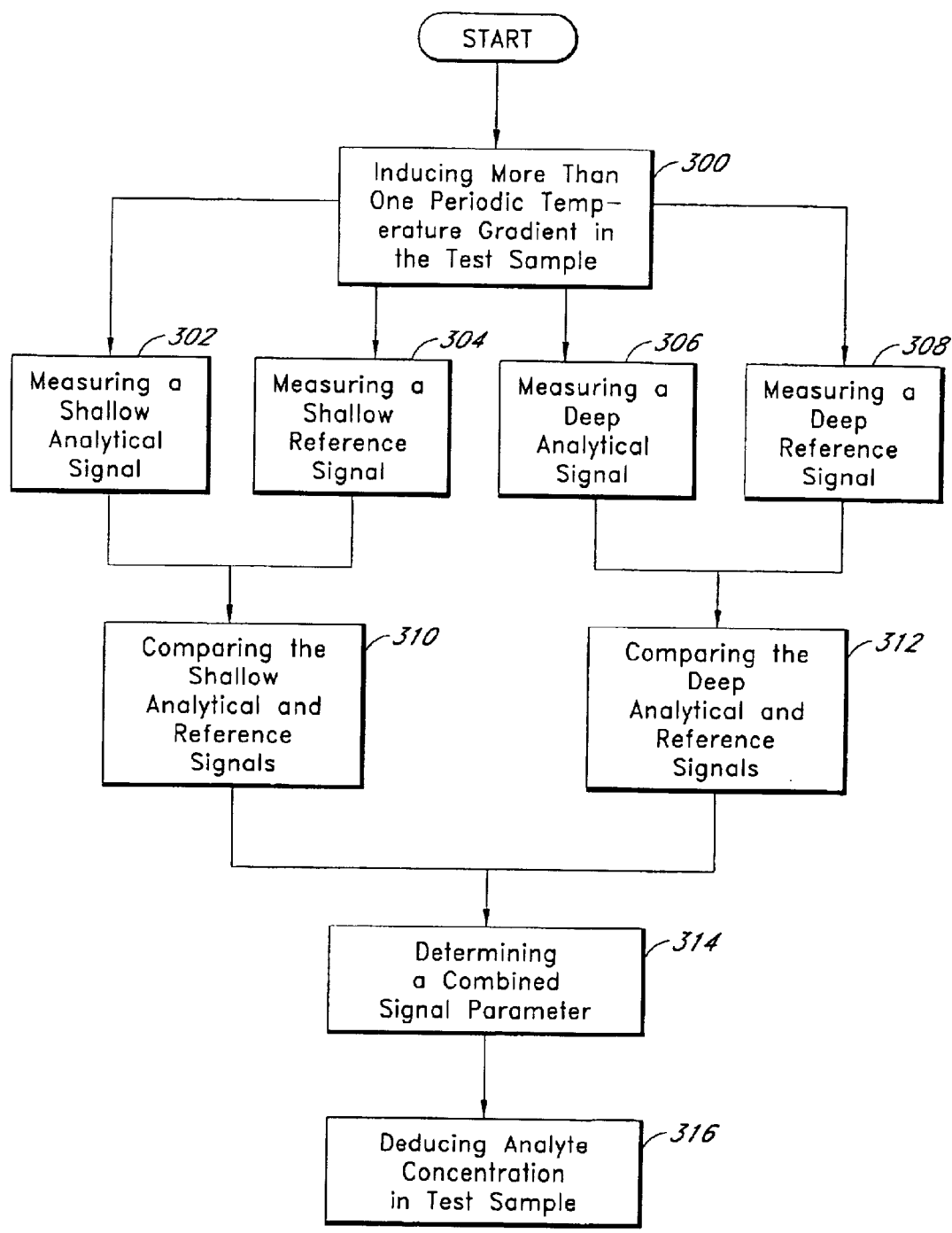
FIG. 20 is a flowchart showing a third embodiment of the present invention.

FIG. 20 is a flowchart depicting an embodiment of the present invention having more than one gradient driving frequency. In Step 300, shallow and deep gradients are cyclically induced in a test sample. In Steps 302, 304, 306, and 308, respectively, measurements are made of a shallow analytical signal 19B', a shallow reference signal 19C, a deep analytical signal 19B, and a deep reference signal 19C. It should be noted that one or more shallow analytical signals 19B', one or more shallow reference signals 19C', one or more deep analytical signals 19B, and a deep reference signals 19C may be measured. In Step 310, the shallow analytical signals 19B' of Step 302 and the shallow reference signals 19C' of Step 304 are compared to form a shallow parameter signal (for example, a shallow phase signal). In Step 312, the deep analytical signals 19B of Step 306 and the deep reference signals 19C of Step 308 are compared to form a deep parameter signal (for example, a deep phase signal). In Step 314 the shallow parameter signal of Step 310 is processed with the deep parameter signal of Step 312 to determine a combined parameter signal. In Step 316 the combined parameter signal of Step 314 is used to deduce the analyte concentration of the test sample.

Figure 21:
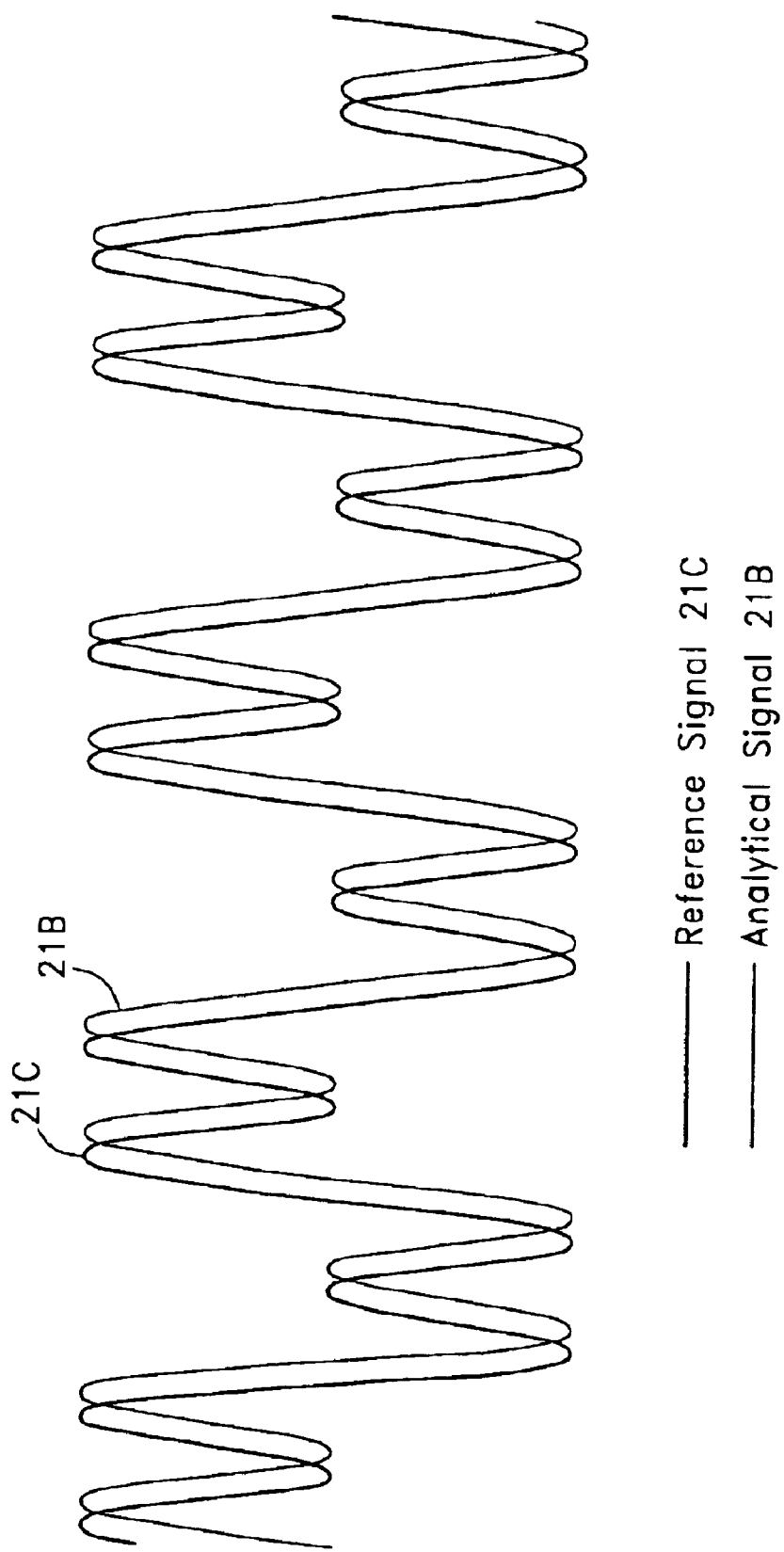
FIG. 21 is a graphical representation of skin response to a two superimposed periodically modulated temperature gradients with the y-axis representing relative detector signal intensity and the x-axis representing the time or phase angle.

Additionally, the two driving frequencies (e.g., 1 Hz and 3 Hz) can be multiplexed as shown in FIG. 21. The fast (3 Hz) and slow (1 Hz) driving frequencies can be superimposed rather than sequentially implemented. During analysis, the signals can be separated by frequency (using Fourier transform or other techniques) using a data processing means and independent measurements of phase delay at each of the two driving frequencies may be calculated. Once resolved, the two signals are processed by a data processing means to determine absorbance and analyte concentration.

E. Embodiment of the Present Invention Using Periodic Gradients Induced at More Than One Driving Frequency to Non-Invasively Determine Human Blood Glucose Concentration.

The present invention may be used to quickly, accurately, and non-invasively determine the blood glucose concentration in a human patient. The gradient driving frequencies may be implemented sequentially (as in FIG. 19) or simultaneously (as in FIG. 21). For illustrative purposes the method of FIG. 19 will be used to determine the blood glucose concentration of a human subject. A first driving frequency is induced at about 1 Hz and penetrates deeply into the fluid containing regions of the skin (e.g. about 150 μm). After a few cycles (preferably two cycles) a second gradient is induced at a second driving frequency. The second frequency is at approximately 3 Hz and induces a shallow gradient which penetrates to just beneath the stratus corneum. After a few cycles (preferably two cycles) a gradient is again induced at the first frequency. In this way the two driving frequencies are alternated over a test period. The test period can be any length of time, but for convenience, a sixty second test period serves well. It should also be noted that the order of implementation of the first and second driving frequencies can be freely altered.

Referring to FIG. 19, the analytical signals 19B, 19B' are measured at a glucose absorbance peak in the range of 7–10 μm. For example, the analytical signal may be monitored using the glucose absorbance peak at 9.3 μm. Reference wavelengths are chosen. As disclosed herein, the signal may be monitored at one or more wavelengths. The reference signal 19C, 19C' shown in FIG. 19 is measured at a water transmission peak, for example, at about 4 μm. The signal when measured at a transmission peak reflects gradient effects deep within the skin. As with all embodiments more then one reference wavelength may be monitored for increased accuracy.

After the first gradient is induced at a first driving frequency a first analytical signal 19B and a first reference signal 19C are monitored. The first analytical signal 19B and the first reference signal 19C are compared. Based on the comparison, a phase difference between the first analytical signal 19B and the first reference signal 19C is measured This phase difference forms a first phase signal $\Phi(\lambda)$ This first phase signal $\Phi(\lambda)$ measures phase differences deeply into the skin, including the stratum corneum. The first phase signal $\Phi(\lambda)$ is monitored as the cooling/heating cycle runs for a predetermined number of cycles.

A second gradient is then induced at a higher frequency (e.g. 1 Hz). This high frequency gradient penetrates to just below the stratum corneum. A second analytical signal 19B' and a second reference signal 19C' are monitored. The second analytical signal 19B' and the second reference signal 19C' are compared. Based on the comparison, a phase difference between the second analytical signal 19B' and the second reference signal 19C' is measured. This phase difference forms a second phase signal $\Phi(\lambda)'$. The second phase signal $\Phi(\lambda)'$ measures phase in the shallow regions of the skin like the stratum corneum. The second phase signal $\Phi(\lambda)'$ is monitored as the cooling/heating cycle runs for a predetermined number of cycles.

The first and second gradients are measured repeatedly over a test period (e.g. about 5–10 seconds). The first phase signal $\Phi(\lambda)$ is subtracted from the second phase signal $\Phi(\lambda)'$ to form a combined phase signal. The combined signal compensates for the effects of the surface and stratum corneum to provide an accurate measure of the phase difference only in the fluid containing regions of the skin, as measured throughout the test period. This combined phase signal information is correlated with previously determined data relating phase to glucose concentration and the concentration of blood glucose in the patient is determined. This patient blood glucose information can be transmitted, as an electrical signal, for further processing.

The present invention discloses a method for measuring radiation absorbance effects and determining analyte concentration in test samples. The procedure has been optimized and illustrated with regard to samples containing large relative quantities of water. The method is widely applicable to homogeneous materials and especially heterogeneous or layered materials provided that useful wavelengths can be identified: (1) a reference wavelength where radiation transmission is high and/or (2) a reference wavelength where radiation transmission is low; (3) analyte absorbance peak where interference with the reference wavelength is low. In particular, the present invention is useful in aqueous systems in the analysis of glucose concentration.

According to a further embodiment of the present invention, the relationship between the modulation of radiation emitted from the surface of a body, for example a human patient, and the modulation of the induced temperature of the surface call be defined in terms of a radiation transfer function. The radiation transfer function depends on absorbance, which, as discussed above depends on the concentration of substances in the tissue. By monitoring the phase and magnitude of the radiation transfer function, the absorbance at selected wavelengths can be determined and from this absorbance the concentration of the analyte is determined.

According to one aspect of this embodiment of the invention the transfer function is developed as follows. It is assumed that a body, for example, the tissue of a patient, in contact with a temperature modulating device is a semi-infinite medium ($0 \leq x < \infty$) in which the temperature, $T(x,t)$, is a function only of the depth and time, and the infrared absorbance of the tissue with a given concentration of an analyte, for example glucose, $\alpha(x,\lambda)$, is a function only of depth and wavelength.

The temperature distribution within the tissue, $T(x,t)$, is governed by the one-dimensional diffusion equation. For a uniform medium, the governing equation is $$\frac{\partial T(x,t)}{\partial t} = \beta \frac{\partial^2 T(x,t)}{\partial x^2},$$

where $\beta$ is the thermal diffusivity [cm$^2$/sec] of the tissue. For sinusoidal temperature modulation, at angular frequency $\omega$ [radians/sec], the equation for the complex amplitude, $\overline{T}(x)$, in a uniform medium, is $$\frac{d^2 \overline{T}(x)}{dx^2} = \frac{i\omega}{\beta} \overline{T}(x).$$

$\overline{T}(x)$ is a complex quantity that specifies the magnitude and phase of the temperature modulation at depth x. The general solution for $\overline{T}(x)$ in a uniform medium is given by $$\overline{T}(x) = Ae^{kx} + Be^{-kx},$$

where $$k = \sqrt{\frac{i\omega}{\beta}} = -(1+i)\gamma \quad \text{and}$$

$$\gamma = \sqrt{\frac{\omega}{2\beta}}.$$

The coefficients. A and B, are determined by the boundary conditions. For example, in a uniform medium extending from zero to infinity, $\overline{T}(x)$ is given by $$\overline{T}(x) = \overline{T}(0) e^{-\gamma x} e^{-i\gamma x}.$$

It is to be noted that the magnitude of the modulation decreases exponentially with depth, and the phase of the modulation decreases linearly with depth. The higher the modulation frequency, the more rapidly magnitude and phase decrease with depth.

The tissue is composed of layers, for example the stratum corneum, stratum lucidum, and deep tissue of a human patient. Within each of theses layers thermal and optical characteristics can be considered uniform. For a layered medium, in which the properties of the medium are constant within each layer a piecewise solution to the diffusion equation is constructed by combining the solutions in each layer with appropriate boundary conditions at the interfaces.

According to one embodiment the surface temperature is sinusoidally modulated with complex amplitude $\overline{T}(0)$ then, because of the linearity of the diffusion equation, the complex amplitude of the temperature at depth x is linearly related to $\overline{T}(0)$ by a complex transfer function, as follows, $$\overline{T}(x) = G(x,\omega) \overline{T}(0).$$

For the case of a semi-infinite uniform medium the transfer function is given by, $$G(x,\omega) = e^{-\gamma x} e^{-i\gamma x},$$

as noted above. For a layered medium, $G(x,\omega)$ is determined by the solution to the diffusion equation with boundary condition $\overline{T}(0)$ at x=0, as well as boundary conditions at surfaces of the layers within the body. According to one aspect of this embodiment, the layers include the stratum corneum, the stratum lucidum and deep tissue of a patient and a piecewise solution to the diffusion equation yields transfer function $G(x,w)$.

As discussed in relation to other embodiments of the invention, as the infrared radiation emitted by deeper layers within the tissue propagates to the surface it is attenuated by the overlying layers. Thus, the radiated power spectral density reaching the surface, at wavelength $\lambda$, can be expressed as $$P(t) = \int_0^\infty dx\, \alpha(x) \exp\left[-\int_0^x d\xi\, \alpha(\xi)\right] \Gamma(T(x,t),\lambda)$$

where $\Gamma(T,\lambda)$ is the Planck radiation function.

$$\Gamma(T,\lambda) = \frac{c_1}{\lambda^5 (e^{c_2/\lambda T} - 1)},$$

where $c_2 = 14{,}380$ $\mu$m K.

It is to be noted that $P(t)$ is just a depth-weighted average of the blackbody function $\Gamma(T(x,t),\lambda)$, with weighting function, $$w(x) = \alpha(x) \exp\left[-\int_0^x d\xi\, \alpha(\xi)\right].$$

The weighting function, $w(x)$, has unit area, independent of the absorbance function, $\alpha(x)$; i.e., $$\int_0^\infty dx\, \alpha(x) \exp\left[-\int_0^x d\xi\, \alpha(\xi)\right] = 1.$$

According to one aspect of this embodiment, the amplitude of the temperature modulation at the surface of the tissue is ±5 K (i.e., ±5° C.) centered about 303 K (i.e., 30°

C.). For small temperature variations in the neighborhood of some constant temperature, $T_0$, an approximation of the Planck radiation function is used as follows:

$$\Gamma(T(x,t),\lambda) \approx \Gamma(T_0,\lambda) + \Gamma_T(T_0,\lambda)[T(x,t)-T_0],$$

where $$\Gamma_T(T,\lambda) = \frac{\partial \Gamma(T,\lambda)}{\partial T}.$$

Yielding $$P(t) = \Gamma(T_0,\lambda) + \Gamma_T(T_0,\lambda) \int_0^\infty dx\, \alpha(x) \exp\left[-\int_0^x d\xi\, \alpha(\xi)\right][T(x,t)-T_0].$$

The first (constant) term is the black body radiation associated with the average temperature, $T_0$. The second term is the response to the time-varying temperature modulation. It is important to note that the time-varying modulation of the radiation is a linear function of the temperature modulation, $T(x,t)-T_0$.

According to one aspect of this embodiment, the surface temperature is sinusoidally modulated in time; i.e., $$T(x,t) = T_0 + T_1(x)\cos(\omega t + \theta(x)).$$

The depth-dependence of the magnitude, $T_1(x)$, and phase $\theta(x)$, will be governed by the diffusion equation. According to the present embodiment $T_1(x) < 10$ K and $T_0 = 303$ K, thus $T_1(x) \ll T_0$, and the linear approximation can be used, and $$P(t) = \Gamma(T_0,\lambda) + \Gamma_T(T_0,\lambda) \int_0^\infty dx\, \alpha(x) \exp\left[-\int_0^x d\xi\, \alpha(\xi)\right][T_1(x)\cos(\omega t + \theta(x))].$$

In dealing with sinusoidal signals it is convenient to use a complex representation.
Thus, $$T_1(x)\cos(\omega t + \theta(x)) = \text{Real}[T_1(x)e^{i\theta(x)}e^{i\omega t}] = \text{Real}[\overline{T}(x)e^{i\omega t}],$$

where $\overline{T}(x) = T_1(x)e^{i\theta(x)}$ is the complex amplitude of $T_1(x)\cos(\omega t + \theta(x))$.
Thus, $$P(t) = \Gamma(T_0,\lambda) + \text{Real}\left[\Gamma_T(T_0,\lambda)\int_0^\infty dx\, \alpha(x)\exp\left[-\int_0^x d\xi\, \alpha(\xi)\right][\overline{T}(x)e^{i\omega t}]\right],$$

or, $$P(t) = \Gamma(T_0,\lambda) + \text{Real}[\overline{P}e^{i\omega t}],$$

where, $$\overline{P} = \Gamma_T(T_0,\lambda)\int_0^\infty dx\, \alpha(x)\exp\left[-\int_0^x d\xi\, \alpha(\xi)\right]\overline{T}(x),$$

is the complex amplitude of the sinusoidal component of $P(t)$.

Thus, the complex amplitude of the modulated radiation (i.e., its magnitude and phase) is a linear function of the complex amplitude (magnitude and phase) of the temperature modulation.

Now, as noted above, $\overline{T}(x)$ is related to the modulation at the surface, $\overline{T}(0)$, by a transfer function; i.e., $$\overline{T}(x) = G(x,\omega)\overline{T}(0)$$

Thus, $$\overline{P} = \Gamma_T(T_0,\lambda)\int_0^\infty dx\, \alpha(x)\exp\left[-\int_0^x d\xi\, \alpha(\xi)\right]G(x,\omega)\overline{T}(0),$$

or, $$\overline{P} = H(\omega,\lambda)\overline{T}(0),$$

where $$H(\omega,\lambda) = \Gamma_T(T_0,\lambda)\int_0^\infty dx\, \alpha(x)\exp\left[-\int_0^x d\xi\, \alpha(\xi)\right]G(x,\omega).$$

The complex quantity, $H(\omega,\lambda)$, is the radiation transfer function from the surface temperature modulation, $\overline{T}(0)$, to the radiation modulation, $\overline{P}$. Both the magnitude and phase of $H(\omega,\lambda)$ are functions of the thermal and infrared properties of the medium. Of particular interest for the estimation of the concentration of substances within tissue is the dependence of $H(\omega,\lambda)$ on the absorbance, $\alpha(x)$. Changes in substance concentration, for example glucose concentration, affect the absorbance spectrum of the medium, and thereby affect both the magnitude and phase of $H(\omega,\lambda)$. By controlling the surface temperature modulation, $\overline{T}(0)$, and measuring the magnitude and phase of the resulting radiation, $\overline{P}$, at various wavelengths, correlations with glucose concentration are obtained. Mathematical models, simulation and experiment have shown that for glucose concentrations in the range of interest, the phase differences between the modulated radiation at two different wavelengths (for which glucose has a different absorbance) is an approximate linear function of glucose concentration.

According to a further embodiment of the invention, a temperature inducing apparatus is controlled by a signal processor to heat and cool the surface of a patient's skin. The signal processor is connected with an optical detector that monitors emitted infrared radiation from the skin surface at a number of discrete wavelengths using, for example, a number of band-pass filters. The signal processor includes the transfer function $H(\omega,\lambda)$ as discussed above. The transfer function may be a model transfer function based on expected values for infrared absorbance, diffusivity, and thermal conductivity for human tissue.

According to one alternative, the model transfer function is stored as an element of a database of model transfer functions at a central location, for example, a file server connected with a communication network such as the Internet. The signal processor is equipped with a telecommunications device, such as a telephone modem, for accessing the database and for retrieving the model transfer function. Model transfer functions stored in the file server include transfer functions for particular types of patients, based for example, on patient's skin color, weight, age, level of physical activity, on the presence of other diseases or medicines in the body that might complicate measurement of glucose, and the like. According to this embodiment, the signed processor selects from the database a selected model transfer function based on a patient's response to questions. The selected model transfer function is then used to correlate the modulation of the radiation emitted from the patient's skin with the modulation of the surface temperature induced in the skin surface to determine glucose concentration. Such a system has the benefit that, as more accurate model transfer functions are developed, these can be added to the database. Furthermore, as a patients condition changes, for example as he gains or loses weight, a different transfer function is selected, thus compensating for variations in the patient's condition.

Alternatively, the transfer function $H(\omega,\lambda)$ may be developed from measurements of a particular patient at a time when the patients glucose level is known using a known technique; for example, analysis of a blood sample using transmission spectrophotometry. According to this embodiment, the phase modulation of the emitted radiation at the discrete wavelengths is compared with the expected modulation based on the transfer function $H(\omega,\lambda)$ and the difference in phase modulation is used to determine a value for glucose concentration based on a known relation between absorbance, $\alpha$ (x) and concentration. According to a further alternative, the transfer function is stored in the database, described above, along with other transfer functions developed empirically from the particular patient, or from other patients having similar demographics, different demographics, or a combination thereof and accessed via the modem.

It should be understood that, while a transfer function developed using a rigorous mathematical treatment of thermal response and radiation absorption is described, more approximate representations of the transfer function may also be used based, for example, on a power series approximation.

In operation, the skin surface temperature is continually cycled at a 1 Hz. rate. Radiation emitted from the skin surface is monitored by an optical detector at a number of predetermined wavelengths, for example 9.25 $\mu$m or 9.65 $\mu$m, where glucose absorbs strongly and 8.45 $\mu$m where glucose absorbs weakly as can be seen from the spectrum of glucose, when dissolved in water, shown in FIG. 11. Both of the absorbance maxima at 9.25 and at 9.65 $\mu$m are appropriate for quantification. These absorbances can be referenced to the absorbances at a wavelength band such as 8.45 $\mu$m, where the glucose absorbance is minimal. At each of these wavelengths water absorbs almost equally, as shown in FIG. 9.

The periodic temperature cycling produces a corresponding periodic signal detected by the detector at each of the predetermined wavelengths. Both magnitude and phase differences of the detector signals are correlated to spectral absorbance and with the application of conventional spectroscopy, converted to glucose concentration.

Figure 22A:
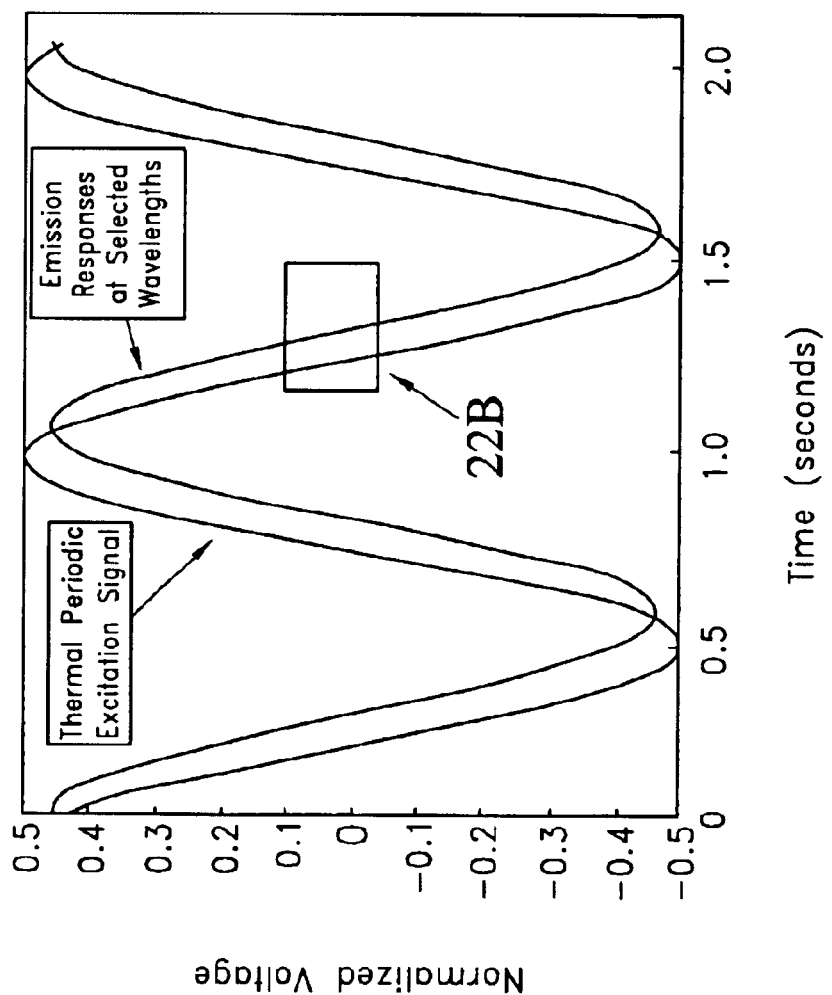
FIGS. 22a and 22b are graphs showing a phase relationship between a surface temperature modulation and emitted radiation at selected infrared wavelengths.
Figure 22B:
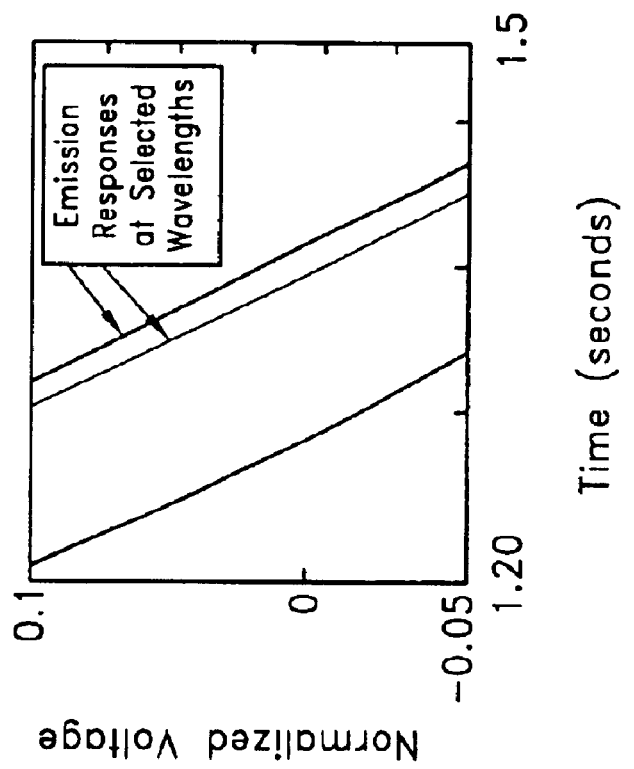

An example of actual signals acquired from two detector channels operated according to an aspect of this embodiment of the invention is shown in FIGS. 22a and 22b. FIG. 22a shows the emission responses at the optical wavelengths 9.25 $\mu$m and 8.45 $\mu$m are phase shifted relative to a sinusoidal thermal excitation drive function for a sample composed of water with 520 mg/dL glucose. The phase shift of the emission response relative to the thermal drive function is a function of the transfer function $H(\omega,\lambda)$ FIG. 22b is a detailed view of a portion of the signals shown in FIG. 22b showing the phase difference between the two IR signals.

Figure 23:
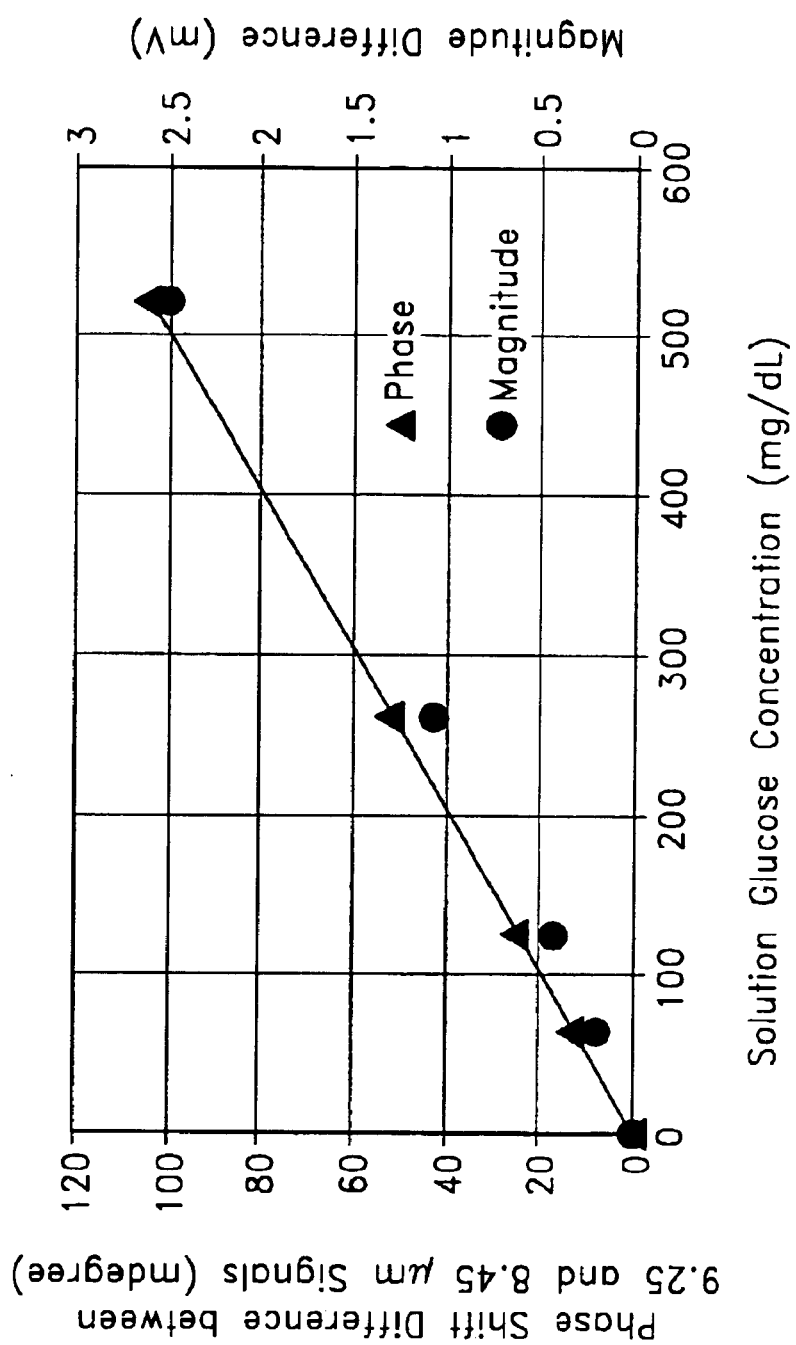
FIG. 23 is a graph showing a correlation between phase shift or signal magnitude and actual glucose concentration measured using a device according to an embodiment of the present invention.
Figure 24:
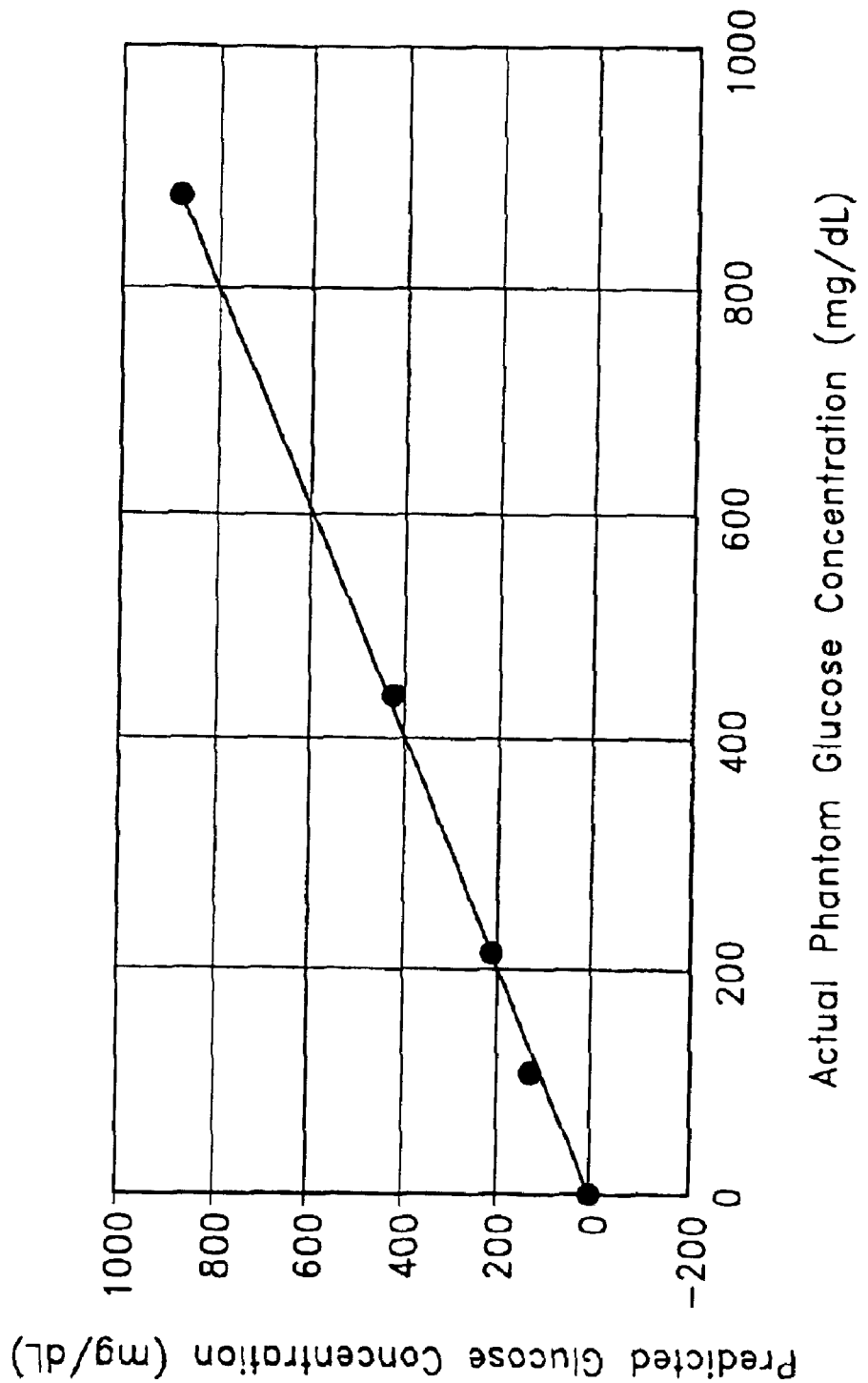
FIG. 24 is a graph showing actual glucose concentrations and glucose concentrations measured using a device according to an embodiment of the invention for a series of skin phantoms.

The phase shift and magnitude results of a series of different glucose concentrations in water are shown in FIG. 23. The line drawn through the data is a regression line. The average glucose error was calculated to be 2 mg/dL. The observed sensitivity was 0.2 millidegrees of phase shift per mg/dL of glucose. A series of tissue "phantoms" were prepared to represent the mechanical properties of skin, as well as the protein and water content of human tissue. Employing phase information from the series of tissue phantoms of varying glucose-equivalent concentration, a linear dose-response relationship between glucose and phase shift was developed. The linear calibration equation, relating phase shift difference to glucose concentration, obtained from glucose/water phase shift data, was applied to the phantom phase shift data. FIG. 24 shows the correlation between the predicted glucose concentration determined from the measured phase shift and the actual glocuse concentration in the prepared phantoms.

The present invention has been shown and described with regard to certain preferred embodiments. However, it should be readily apparent to those of ordinary skill in the art that various changes and modifications in form or detail may be made with departure from the spirit and scope of the disclosure, as set forth, which embodiments are provided for purpose of illustration and not of limitation. For example, the invention disclosed herein is not limited to detection of ethanol or glucose, but may be used to quantify an analyte concentration of a wide variety of analytes. Furthermore, the invention is not confined to use on a test sample that is an in-vivo human subject but rather may be used on other tests samples such as animals in-vivo and plants as well as on in-vitro test samples.

We claim:

1. A method for detecting a concentration of a substance in a body, the method comprising:
   inducing a time-varying temperature on a surface of the body, the temperature varying according to a surface temperature modulation;
   detecting radiation emitted from the surface of the body, the emitted radiation having an emitted radiation modulation;
   defining a first transfer function relating the emitted radiation modulation to (i) the surface temperature modulation and (ii) an absorbance; and
   determining the absorbance based on the first transfer function.

2. The method of claim 1, further comprising determining a phase or a magnitude of the first transfer function based on the emitted radiation modulation and the surface temperature modulation.

3. The method of claim 1, further comprising determining the substance concentration based on the absorbance.

4. The method of claim 1, further comprising defining a second transfer function relating the surface temperature modulation with a depth-dependent temperature modulation within the body, wherein the body includes a plurality of layers and wherein the second transfer function comprises a piecewise solution to a thermal diffusion equation.

5. The method according to claim 1, wherein the surface temperature modulation is sinusoidal.

6. The method according to claim 1, wherein detecting comprises monitoring radiation at a plurality of discrete wavelengths.

7. An apparatus for detecting a concentration of a substance in a body, the apparatus comprising:
   a thermal device adapted to induce a time-varying temperature on a body surface;
   a detector adapted to detect radiation emitted from the body surface, the emitted radiation having an emitted radiation modulation;
   a controller configured to drive the thermal device such that the time-varying temperature varies according to a surface temperature modulation; and a signal processor connected to the detector and adapted to detect a phase and magnitude of the emitted radiation modulation, the signal processor including a transfer function that relates the surface temperature modulation to the emitted radiation modulation.

8. The apparatus according to claim 7, wherein the signal processor determines an expected emitted radiation modulation based on the transfer function and compares said expected emitted radiation modulation with the detected emitted radiation modulation.

9. The apparatus according to claim 7, wherein the transfer function comprises a function based on nominal values of constituent variables expected in the body.

10. The apparatus according to claim 7, wherein the transfer function comprises predetermined values corresponding to values measured in the body under known conditions.

11. The apparatus according to claim 7, wherein the thermal device is a heating device.

12. The apparatus according to claim 7, wherein the thermal device is a cooling device.

13. A method for determining an optical absorbance of a tissue comprising:

determining a thermal transfer function that relates a tissue surface temperature modulation to an internal tissue temperature modulation;

detecting radiation emitted from the tissue, the emitted radiation having an emitted radiation modulation;

defining a radiation transfer function that relates the emitted radiation modulation to the internal tissue temperature modulation, the radiation transfer function including the optical absorbance; and determining a correlation between a phase or magnitude of the radiation transfer function and the optical absorbance.

14. The method of claim 13, further comprising determining a concentration of a substance in the tissue as a function of the determined optical absorbance.

15. An apparatus for detecting a concentration of a substance in a body, the apparatus comprising:

a thermal device adapted to induce a time-varying temperature on a body surface;

a detector adapted to detect radiation emitted from the body surface, the emitted radiation having an emitted radiation modulation;

a controller configured to drive the thermal device such that the time-varying temperature varies according to a surface temperature modulation; and a signal processor connected to the detector and adapted to detect a phase and magnitude of the emitted radiation modulation, the signal processor including a plurality of model transfer functions that relate to a respective plurality of model responses between the surface temperature modulation and the emitted radiation modulation, wherein each model transfer function depends on a set of patient parameters.

16. The apparatus of claim 15, wherein the plurality of model transfer functions are stored in a memory.

17. The apparatus of claim 16, further comprising a communication device configured to connect the signal processor with the memory and to communicate a selected model transfer function to the signal processor, wherein the signal processor determines the concentration of the substance based on (i) the phase and magnitude of the emitted radiation modulation relative to the surface temperature modulation and (ii) the selected model transfer function.

18. The apparatus according to claim 17, wherein the communication device comprises a network adapted to communicate data between the memory at a first location and the signal processor at a second location.

19. The apparatus according to claim 18, wherein the network comprises the internet.

20. The apparatus according to claim 15, wherein the set of patient parameters comprise factors describing conditions of a human subject and wherein the body surface is a skin surface of a patient.

21. The apparatus according to claim 20, further comprising a computing device configured to select a model transfer function based on responses to questions regarding conditions of the patient.

22. A method for detecting a concentration of a substance in a body, the method comprising:

inducing a time-varying temperature on a surface of the body, the temperature varying according to a surface temperature modulation;

detecting radiation emitted from the surface of the body, the emitted radiation having an emitted radiation modulation; and determining an absorbance based on a first transfer function which relates the emitted radiation modulation to (i) the surface temperature modulation and (ii) the absorbance.

23. The method of claim 22, further comprising determining a phase or a magnitude of the first transfer function based on the emitted radiation modulation and the surface temperature modulation.

24. The method of claim 22, further comprising determining the substance concentration based on the absorbance.

25. The method of claim 22, further comprising defining a second transfer function relating the surface temperature modulation with a depth-dependent temperature modulation within the body, wherein the body includes a plurality of layers and wherein the second transfer function comprises a piecewise solution to a thermal diffusion equation.

26. The method according to claim 22, wherein the surface temperature modulation is sinusoidal.

27. The method according to claim 22, wherein detecting comprises monitoring radiation at a plurality of discrete wavelengths.

* * * * *